(12) United States Patent
Nettekoven et al.

(10) Patent No.: US 6,689,790 B2
(45) Date of Patent: Feb. 10, 2004

(54) SUBSTITUTED TRIAZOLOPYRIDINE COMPOUNDS

(75) Inventors: Matthias Heinrich Nettekoven, Grenzack-Wyhlen (DE); Sebastien Schmitt, St. Louis (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 24 days.

(21) Appl. No.: 10/265,957

(22) Filed: Oct. 7, 2002

(65) Prior Publication Data

US 2003/0207911 A1 Nov. 6, 2003

(30) Foreign Application Priority Data

Oct. 8, 2001 (EP) ............................. 01123948

(51) Int. Cl.[7] ..................... A61K 31/437; C07D 471/04; A61P 25/16; A61P 25/24
(52) U.S. Cl. ................. 514/303; 514/228.5; 514/233.5; 544/61; 544/127; 546/120; 546/119
(58) Field of Search ................ 546/120, 119; 544/61, 127; 514/303, 228.5, 233.5

(56) References Cited

U.S. PATENT DOCUMENTS 6,506,772 B1 * 1/2003 Brodbeck .................. 514/303

FOREIGN PATENT DOCUMENTS

| DE | 287263 | * | 2/1991 |
| EP | 0976 753 | | 2/2000 |
| WO | WO 0117999 | | 3/2001 |
| WO | WO 0248145 | | 6/2002 |

OTHER PUBLICATIONS

Poulsen et al., *Bioorganic & Med. Chem.*, vol. 6, pp. 619–641 (1998).
Muller et al., *Bioorganic & Med. Chem.*, vol. 6, pp. 707–719 (1998).
Kim et al., *J. Med. Chem.*, vol. 41, pp. 2835–2845 (1998).
Li et al., *J. Med. Chem.*, vol. 41, pp. 3186–3201 (1998).
Baraldi et al. *J. Med. Chem.*, vol. 41, pp. 2126–2133 (1998).
Li et al., *J. Med. Chem.*, vol. 42, pp. 706–721 (1999).
Baraldi et al., *J. Med. Chem.*, vol. 39, pp. 1164–1171 (1996).
Colotta etal., *Arch. Pharm. Med. Chem.*, vol. 332, pp. 39–41 (1999).

* cited by examiner

*Primary Examiner*—Evelyn Mei Huang
(74) *Attorney, Agent, or Firm*—George W. Johnston; Patricia S. Rocha-Tramaloni; Kimberly J. Prior

(57) ABSTRACT

A compound of formula

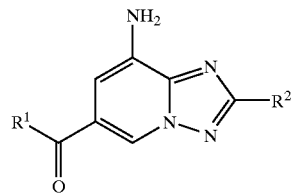

wherein
- $R^1$ is —NR'R", wherein R' and R" are independently selected from the group consisting of lower alkyl, —$(CH_2)_n$—C(O)NR$^a$R$^b$, —$(CH_2)_n$-heteroaryl, —$(CH_2)_n$-aryl, —$(CH_2)_n$—CN, —$(CH_2)_n$—O-lower alkyl or —$(CH_2)_n$-cycloalkyl, or R' and R" form together with the N-atom a five or six-membered non-aromatic ring, containing no or one additional heteroatom selected from the group consiting of
- O and S, and said ring being unsubstituted or substituted by one or two substituents, selected from the group consisting of lower alkyl, —C(O)NR$^a$R$^b$ and —$(CH_2)_n$—O-lower alkyl, and R$^a$R$^b$ are independently from each other hydrogen or lower alkyl;
- $R^2$ is aryl or heteroaryl, unsubstituted or substituted by lower alkyl or halogen; and
- n is 0, 1, 2 or 3;

or a pharmaceutically acceptable salt thereof. Compounds of formula I are useful in the treatment of disease associated with the adenosine A2 receptor.

16 Claims, No Drawings

SUBSTITUTED TRIAZOLOPYRIDINE COMPOUNDS

FIELD OF INVENTION

The present invention relates to a compound of the formula

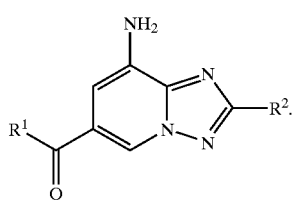

I

This compound is an adenosine receptor ligand useful in the control or prevention of illnesses modulated by the adenosine system, such as, for example, Alzheimer's disease and Parkinson's disease.

BACKGROUND

Adenosine modulates a wide range of physiological functions by interacting with specific cell surface receptors. The potential of adenosine receptors as drug targets was first reviewed in 1982. Adenosine is related both structurally and metabolically to the bioactive nucleotides adenosine triphosphate (ATP), adenosine diphosphate (ADP), adenosine monophosphate (AMP) and cyclic adenosine monophosphate (cAMP); to the biochemical methylating agent S-adenosyl-L-methione (SAM); and structurally to the coenzymes NAD, FAD and coenzyme A; and to RNA. Together adenosine and these related compounds are important in the regulation of many aspects of cellular metabolism and in the modulation of different central nervous system activities.

The receptors for adenosine have been classified as $A_1$, $A_{2A}$, $A_{2B}$ and $A_3$ receptors, belonging to the family of G protein-coupled receptors. Activation of adenosine receptors by adenosine initiates signal transduction mechanism. These mechanisms are dependent on the receptor associated G protein. Each of the adenosine receptor subtypes has been classically characterized by the adenylate cyclase effector system, which utilizes cAMP as a second messenger. The $A_1$ and $A_3$ receptors, coupled with $G_i$ proteins inhibit adenylate cyclase, leading to a decrease in cellular cAMP levels, while $A_{2A}$ and $A_{2B}$ receptors couple to G, proteins and activate adenylate cyclase, leading to an increase in cellular cAMP levels. It is known that the $A_1$ receptor system include the activation of phospholipase C and modulation of both potassium and calcium ion channels. The $A_3$ subtype, in addition to its association with adenylate cyclase, also stimulates phospholipase C and so activates calcium ion channels.

The $A_1$ receptor (326–328 amino acids) was cloned from various species (canine, human, rat, dog, chick, bovine, guinea-pig) with 90–95% sequence identify among the mammalian species. The $A_{2A}$ receptor (409–412 amino acids) was cloned from canine, rat, human, guinea pig and mouse. The $A_{2B}$ receptor (332 amino acids) was cloned from human and mouse with 45% homology of human $A_{2B}$ with human $A_1$ and $A_{2A}$ receptors. The $A_3$ receptor (317–320 amino acids) was cloned from human, rat, dog, rabbit and sheep.

The $A_1$ and $A_{2A}$ receptor subtypes are proposed to play complementary roles in adenosine's regulation of the energy supply. Adenosine, which is a metabolic product of ATP, diffuses from the cell and acts locally to activate adenosine receptors to decrease the oxygen demand ($A_1$) or increase the oxygen supply ($A_{2A}$) and so reinstate the balance of energy supply versus demand within the tissue. The actions of both subtypes is to increase the amount of available oxygen to tissue and to protect cells against damage caused by a short-term imbalance of oxygen. One of the important functions of endogenous adenosine is preventing damage during traumas such as hypoxia, ischaemia, hypotension and seizure activity.

Furthermore, it is known that the binding of the adenosine receptor agonist to mast cells expressing the rat $A_3$ receptor resulted in increased inositol triphosphate and intracellular calcium concentrations, which potentiated antigen induced secretion of inflammatory mediators. Therefore, the $A_3$ receptor plays a role in mediating asthmatic attacks and other allergic responses.

Adenosine is also a neuromodulator, possessing global importance in the modulation of molecular mechanisms underlying many aspects of physiological brain function by mediating central inhibitory effects. An increase in neurotransmitter release follows traumas such as hypoxia, ischaemia and seizures. These neurotransmitters are ultimately responsible for neural degeneration and neural death, which causes brain damage or death of the individual. The adenosine $A_1$ agonists which mimic the central inhibitory effects of adenosine may therefore be useful as neuroprotective agents. Adenosine has been proposed as an endogenous anticonvulsant agent, inhibiting glutamate release from excitory neurons and inhibiting neuronal firing. Adenosine agonists therefore may be used as antiepileptic agents. Adenosine antagonists stimulate the activity of the CNS and have proven to be effective as cognition enhancers. Selective $A_{2a}$-antagonists have therapeutic potential in the treatment of various forms of dementia, for example in Alzheimer's disease and are useful as neuroprotective agents. Adenosine $A_2$-receptor antagonists inhibit the release of dopamine from central synaptic terminals and reduce locomotor activity and consequently improve Parkinsonian symptoms. The central activities of adenosine are also implicated in the molecular mechanism underlying sedation, hypnosis, schizophrenia, anxiety, pain, respiration, depression and substance abuse. Drugs acting at adenosine receptors therefore have also therapeutic potential as sedatives, muscle relaxants, antipsychotics, anxiolytics, analgesics, respiratory stimulants and antidepressants.

An important role for adenosine in the cardiovascular system is as a cardioprotective agent. Levels of endogenous adenosine increase in response to ischaemia and hypoxia, and protect cardiac tissue during and after trauma (preconditioning). Adenosine agonists thus have potential as cardioprotective agents.

Adenosine modulates many aspects of renal function, including renin release, glomerular filtration rate and renal blood flow. Compounds, which antagonize the renal affects of adenosine, have potential as renal protective agents. Furthermore, adenosine $A_3$ and/or $A_{2B}$ antagonists may be useful in the treatment of asthma and other allergic responses.

Numerous documents describe the current knowledge on adenosine receptors, for example the following publications:

Bioorganic & Medicinal Chemistry, 6, (1998), 619–641,
Bioorganic & Medicinal Chemistry, 6, (1998), 707–719,
J. Med. Chem., (1998), 41, 2835–2845,
J. Med. Chem., (1998), 41, 3186–3201, J. Med. Chem., (1998), 41, 2126–2133,
J. Med. Chem., (1999), 42, 706–721,
J. Med. Chem., (1996), 39, 1164–1171,
Arch. Pharm. Med. Chem., (1999), 332, 39–41.

SUMMARY

The present invention is a compound of formula

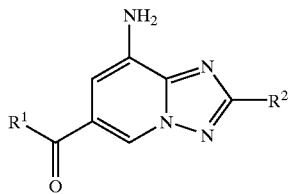

wherein
R$^1$ is —NR'R", wherein R' and R" are independently selected from the group consisting of lower alkyl, —(CH$_2$)$_n$—C(O)NR$^a$R$^b$, —(CH$_2$)$_n$-heteroaryl, —(CH$_2$)$_n$-aryl, —(CH$_2$)$_n$—CN, —(CH$_2$)$_n$—O-lower alkyl or —(CH$_2$)$_n$-cycloalkyl, or R' and R" form together with the N-atom a five or six-membered non-aromatic ring, containing no or one additional heteroatom selected from the group O and S, said ring being unsubstituted or substituted by one or two substituents, selected from the group consisting of lower alkyl, —C(O)NR$^a$R$^b$ or —(CH$_2$)$_n$—O-lower alkyl and R$^a$R$^b$ are independently from each other hydrogen or lower alkyl;

R$^2$ is aryl or heteroaryl, unsubstituted or substituted by lower alkyl or halogen; and n is 0, 1, 2 or 3;

or a pharmaceutically acceptable salt thereof.

It has surprisingly been found that the compounds of formula I are adenosine receptor ligands.

Compounds of the present invention of formula I and their pharmaceutically acceptable salts are pharmaceutically active substances. The present invention includes a process for the manufacture of compounds of formula I and pharmaceutical compositions comprising a therapeutically effective amount of at least one compound of formula I and an excipient. The present invention is also directed to a method of controlling or preventing illnesses based on the modulation of the adenosine system, such as Alzheimer's disease, Parkinson's disease, neuroprotection, schizophrenia, anxiety, pain, respiration deficits, depression, asthma, allergic responses, hypoxia, ischaemia, seizure and substance abuse by administering a therapeutically effective amount of a compound of formula I to patient in need of such treatment. Furthermore, compounds of the present invention may be useful as sedatives, muscle relaxants, antipsychotics, antiepileptics, anticonvulsants and cardioprotective agents. The most preferred indications in accordance with the present invention are those, which base on the A$_{2A}$ receptor antagonistic activity and which include disorders of the central nervous system, for example the treatment or prevention of certain depressive disorders, neuroprotection and Parkinson's disease.

DETAILED DESCRIPTION OF THE INVENTION

As used herein, the term "lower alkyl" denotes a saturated straight- or branched-chain alkyl group containing from 1 to 6 carbon atoms, for example, methyl, ethyl, propyl, isopropyl, n-butyl, i-butyl, 2-butyl, t-butyl and the like. Preferred lower alkyl groups are groups with 1–4 carbon atoms.

The term "cycloalkyl" denotes a saturated carbocyclic group, containing 3–8 carbon atoms. A preferred cycloalkyl group is cyclohexyl.

The term "halogen" denotes chlorine, iodine, fluorine and bromine.

The term "lower alkoxy" denotes a group wherein the alkyl residues is as defined above, and which is attached via an oxygen atom.

The term "aryl" denotes phenyl or naphthyl. The preferred aryl group is phenyl.

The term "heteroaryl" denotes 5 or 6 membered rings with heteroatoms, such as O, N or S, for example, pyridinyl, thiophenyl, furanyl or thiazolyl.

The term "5 or 6 membered non-aromatic ring" denotes 5- or 6-membered rings, which may contain one additional heteroatom, such as O or S, in addition to the N atom, for example morpholinyl, thiomorpholinyl, piperidinyl, pyrrolidinyl or 3,6-dihydro-2H-pyridin-1-yl.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

A compound of formula I of the present invention, wherein R$^2$ is heteroaryl, such as furan-2-yl, substituted by bromo, is preferred. A preferred compound of this embodiment is selected from the group consisting of:

[8-Amino-2-(5-bromo-furan-2-yl)-[1,2,4]triazolo[1,5-a]pyridin-6-yl]-piperidin-1-yl-methanone,

[8-amino-2-(5-bromo-furan-2-yl)-[1,2,4]triazolo[1,5-a]pyridin-6-yl]-methanone,

[8-amino-2-(5-bromo-furan-2-yl)-[1,2,4]triazolo[1,5-a]pyridin-6-yl]-pyrrolidin-1-yl)-methanone, 1-[8-amino-2-(5-bromo-furan-2-yl)-[1,2,4]triazolo[1,5-a]pyridine-6-carbonyl]-piperidine-3-carboxylic acid diethylamide,

[8-amino-2-(5-bromo-furan-2-yl)-[1,2,4]triazolo[1,5-a]pyridin-6-yl]-(3,5-dimethyl-piperidin-1-yl)-methanone,

[8-amino-2-(5-bromo-furan-2-yl)-[1,2,4]triazolo[1,5-a]pyridin-6-yl]-(2-methyl-piperidin-1-yl)-methanone,

[8-amino-2-(5-bromo-furan-2-yl)-[1,2,4]triazolo[1,5-a]pyridin-6-yl]-(2-methoxymethyl-pyrrolidin-1-yl)-methanone,

[8-amino-2-(5-bromo-furan-2-yl)-[1,2,4]triazolo[1,5-a]pyridin-6-yl]-((S)-2-methoxymethyl-pyrrolidin-1-yl)-methanone, 1-[8-amino-2-(5-bromo-furan-2-yl)-[1,2,4]triazolo[1,5-a]pyridine-6-carbonyl]-pyrrolidine-2-carboxylic acid (S)-dimethylamide, 8-amino-2-(5-bromo-furan-2-yl)-[1,2,4]triazolo[1,5-a]pyridine-6-carboxylic acid dimethylcarbamoylmethyl-methyl-amide,

[8-amino-2-(5-bromo-furan-2-yl)-[1,2,4]triazolo[1,5-a]pyridin-6-yl]-(3-methyl-piperidin-1-yl)-methanone, 8-amino-2-(5-bromo-furan-2-yl)-[1,2,4]triazolo[1,5-a]pyridine-6-carboxylic acid methyl-propyl-amide, 8-amino-2-(5-bromo-furan-2-yl)-[1,2,4]triazolo[1,5-a]pyridine-6-carboxylic acid ethyl-(2-pyridin-2-yl-ethyl)-amide,

[8-amino-2-(5-bromo-furan-2-yl)-[1,2,4]triazolo[1,5-a]pyridin-6-yl]-thiomorpholin-4-yl-methanone and 8-amino-2-(5-bromo-furan-2-yl)-[1,2,4]triazolo[1,5-a]pyridine-6-carboxylic acid methyl-phenethyl-amide.

A further preferred compound of formula I of the present invention is, wherein $R^2$ is unsubstituted heteroaryl, such as furan-2-yl. An example of this preferred compound is selected from the group consisting of:

(8-Amino-2-furan-2-yl-[1,2,4]triazolo[1,5-a]pyridin-6-yl)-pyrrolidin-1-yl-methanone, (8-amino-2-furan-2-yl-[1,2,4]triazolo[1,5-a]pyridin-6-yl)-(2-R-methoxymethyl-pyrrolidin-1-yl)-methanone, (8-amino-2-furan-2-yl-[1,2,4]triazolo[1,5-a]pyridin-6-yl)-(2-S-methoxymethyl-pyrrolidin-1-yl)-methanone and 8-amino-2-furan-2-yl-[1,2,4]triazolo[1,5-a]pyridine-6-carboxylic acid dibenzylamide.

A compound of formula I of the present invention, wherein $R^2$ is heteroaryl, such as thiophen-2-yl, is also preferred. Exemplary of this preferred compound is 8-Amino-2-thiophen-2-yl-[1,2,4]triazolo[1,5-a]pyridine-6-carboxylic acid dibenzylamide.

A further preferred compound is wherein $R^2$ is heteroaryl, such as furan-2-yl, substituted by methyl. A compound exemplary of this preferred compound is selected from the group consisting of:

[8-Amino-2-(5-methyl-furan-2-yl)-[1,2,4]triazolo[1,5-a]pyridin-6-yl]-pyrrolidin-1-yl-methanone,

[8-amino-2-(5-methyl-furan-2-yl)-[1,2,4]triazolo[1,5-a]pyridin-6-yl]-piperidin-1-yl-methanone,

[8-amino-2-(5-methyl-furan-2-yl)-[1,2,4]triazolo[1,5-a]pyridin-6-yl]-(2-methyl-pyrrolidin-1-yl)-methanone and 8-amino-2-(5-methyl-furan-2-yl)-[1,2,4]triazolo[1,5-a]pyridine-6-carboxylic acid methyl-propyl-amide.

A compound of formula I of the present invention or a pharmaceutically acceptable salt thereof can be prepared by methods known in the art, for example, by processes described below, which process comprises reacting a compound of formula

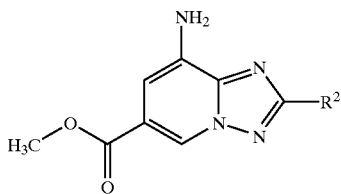

II with an amine of formula

HNR'R"    III to a compound of formula

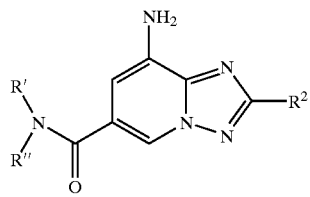

I wherein R', R" and $R^2$ have the significance given above, and converting the compounds obtained into a pharmaceutically acceptable acid addition salt by reaction with a sufficient quantity of a pharmaceutically acceptable acid.

In accordance with the above mentioned process variant for obtaining a compound of formula I (8-amino-2-(aryl or heteroaryl)-[1,2,4]triazolo[1,5-a]pyridin-6-yl]-piperidin-1-yl-methanone), a solution of an amine of formula III (HNR'R") in dioxane is treated with trimethylaluminum in toluene and stirred for 1 h at room temperature. 8-Amino-2-(aryl or heteroaryl)-[1,2,4]triazolo[1,5-a]pyridine-6-carboxylic acid methyl ester (II) in 1 ml dioxane is added and the mixture is heated to 90° C. for 72 h. HCl aq. is added and the volatiles are removed. The residue is taken up in 1 formic acid and methanol and purified by reversed phase preparative HPLC eluting with a gradient of acetonitrile and water.

Salt formation from a compound of formula I of the present invention is effected at room temperatures in accordance with methods familiar to a person skilled in the art. Pharmaceutically acceptable salts may be formed with pharmaceutically acceptable inorganic acids or organic acids. Hydrochlorides, hydrobromides, sulfates, nitrates, citrate, acetates, maleates, succinates, methane-sulfonates, p-toluenesulfonates and the like are examples of such salts.

In Examples 9–108 and in the following scheme 1 the preparation of compounds of formula I is described in more detail.

Scheme 1

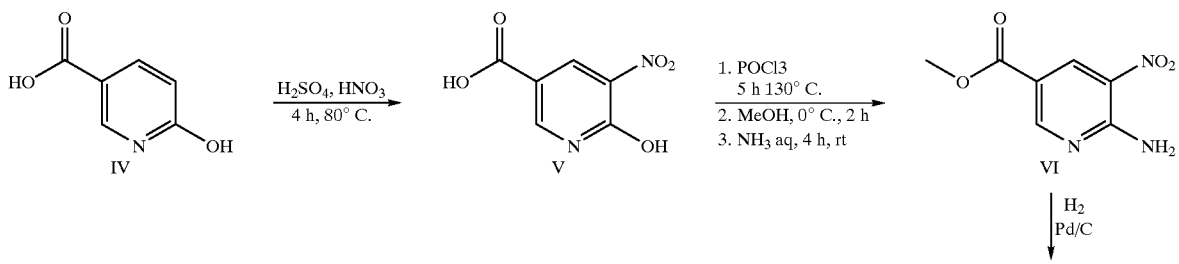

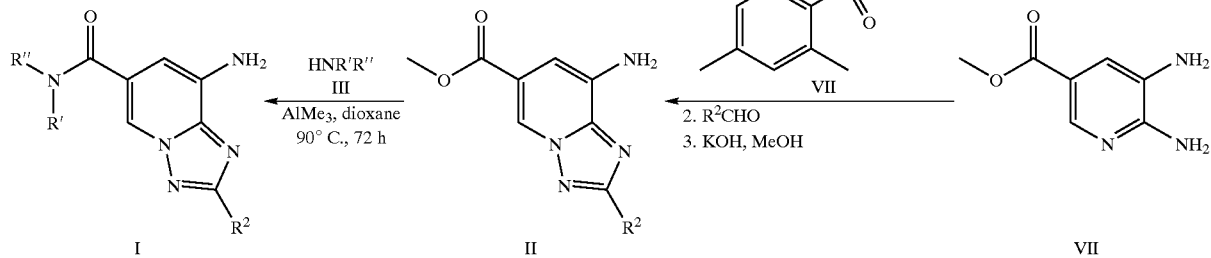

In accordance with scheme 1, the compound of formula V (6-hydroxy-5-nitro-nicotinic acid) is obtained as follows: To a solution of a compound of formula IV (6-hydroxy-nicotinic acid) in concentrated sulfuric acid is added a mixture of concentrated sulfuric acid and concentrated nitric acid below 20° C. and stirred for 1 h at room temperature and afterwards the solution is heated to 80° C. for 4 h. The mixture is then poured onto ice and the precipitate is collected and dried. The obtained compound of formula V is then mixed with POCl$_3$ and heated to 130° C. for 5 h and afterwards the excess POCl$_3$ is distilled under reduced pressure. The residue is cooled to 0° C. and 150 ml methanol were slowly added. The mixture is stirred for 2 h at 0° C. After addition of a 25% NH$_3$ aq. solution the mixture is stirred for 4 h at room temperature. The precipitate is filtered, washed once with diethyl ether and dried under vacuum to yield 6-amino-5-nitro-nicotinic acid methyl ester (VI). A suspension of 6-amino-5-nitro-nicotinic acid methyl ester in methanol and Pd/C (10%) cat is then added and hydrogenated at room temperature during 14 h. The catalyst is filtered off and the solution is concentrated to yield 5,6-diamino-nicotinic acid methyl ester (VII). A mixture of (VII) in dioxane is treated with O-mesitylenesulfonylhydroxylamine (prepared from ethyl-o-mesitylenesulfonylacetohydroxamate and HClO$_4$) for 1 h at room temperature. To thiophene-2-carboxaldehyde or another aldehyde of formula R$^2$CHO, wherein R$^2$ is an aryl or heteroaryl as described in the specification, molecular sieves 4 Å is added and heated to 100° C. for 4 h before addition of KOH in methanol. The mixture is heated to 70° C. for 2 h and stirred at room temperature for 14 h. The volatiles are removed under reduced pressure and the residue is purified by flash column chromatography to yield 8-amino-2-(aryl or heteroaryl)-[1,2,4]triazolo[1,5-a]pyridine-6-carboxylic acid methyl ester (II). To obtain a compound of formula 1 (8-amino-2-(aryl or heteroaryl)-[1,2,4]triazolo[1,5-a]pyridin-6-yl]-piperidin-1-yl-methanone a solution of an amine of formula III (HNR'R'') in dioxane is treated with trimethylaluminum in toluene and stirred for 1 h at room temperature. 8-Amino-2-(aryl or heteroaryl)-[1,2,4]triazolo[1,5-a]pyridine-6-carboxylic acid methyl ester (II) in 1 ml dioxane is added and the mixture is heated to 90° C. for 72 h. HCl aq. is added and the volatiles are removed. The residue is taken up in 1 formic acid and methanol and purified by reversed phase preparative HPLC eluting with a gradient of acetonitrile and water.

The compounds of formula I and their pharmaceutically acceptable addition salts possess valuable pharmacological properties. Specifically, it has been found that the compounds of the present invention are adenosine receptor ligands.

All of the compounds of the examples were investigated in accordance with the tests given hereinafter.

Human Adenosine A$_{2A}$ Receptor

The human adenosine A$_{2A}$ receptor was recombinantly expressed in chinese hamster ovary (CHO) cells using the semliki forest virus expression system. Cells were harvested, washed twice by centrifugation, homogenized and again washed by centrifugation. The final washed membrane pellet was suspended in a Tris (50 mM) buffer containing 120 mM NaCl, 5 mM KCl, 2 mM CaCl$_2$ and 10 mM MgCl$_2$ (pH 7.4) (buffer A). The [$^3$H]-SCH-58261 (Dionisotti et al., 1997, Br. J. Pharmacol. 121, 353) binding assay was carried out in 96-well plates in the presence of 2.5 µg of membrane protein, 0.5 mg of Ysi-poly-1-lysine SPA beads and 0.1 U adenosine deaminase in a final volume of 200 µl of buffer A. Non-specific binding was defined using xanthine amine congener (XAC; 2 µM). Compounds were tested at 10 concentrations from 10 µM–0.3 nM. All assays were conducted in duplicate and repeated at least two times. Assay plates were incubated for 1 hour at room temperature before centrifugation and then bound ligand determined using a Packard Topcount scintillation counter. IC$_{50}$ values were calculated using a non-linear curve fitting program and K$_i$ values calculated using the Cheng-Prussoff equation.

In accordance with the invention, it has been shown that compounds of formula I have a high affinity toward the A$_{2A}$ receptor. In the table below are described specific values of prepared compounds. Preferred compounds are those, wherein the hA2a K$_i$ is less than 100 nM, foe example the followings:

| Example No. | hA2a K$_i$ (nM) |
| --- | --- |
| 11 | 35.2 |
| 12 | 26.8 |
| 13 | 40.5 |
| 14 | 37.2 |
| 15 | 62.4 |
| 16 | 16.4 |
| 17 | 61.2 |
| 18 | 67.0 |
| 19 | 23.2 |
| 20 | 15.5 |
| 21 | 44.6 |
| 22 | 76.2 |
| 25 | 50.0 |
| 34 | 56.8 |
| 37 | 34.9 |
| 41 | 77.6 |
| 42 | 69.4 |
| 64 | 83.0 |
| 83 | 75.6 |
| 84 | 56.8 |

-continued

| Example No. | hA2a K$_i$ (nM) |
|---|---|
| 85 | 75.2 |
| 88 | 56.2 |

The compounds of formula I and the pharmaceutically acceptable salts of the compounds of formula I can be used in pharmaceutical compositions, e.g. in the form of pharmaceutical preparations. The pharmaceutical preparations can be administered orally, e.g. in the form of tablets, coated tablets, dragées, hard and soft gelatin capsules, solutions, emulsions or suspensions. The administration can, however, also be effected rectally, e.g. in the form of suppositories, parenterally, e.g. in the form of injection solutions.

The compounds of formula I can be processed with pharmaceutically inert, inorganic or organic carriers for the production of pharmaceutical preparations. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical preparations can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

Pharmaceutical compositions containing a compound of formula I or a pharmaceutically acceptable salt thereof and a therapeutically inert carrier are also an object of the present invention, as is a process for their production, which comprises bringing one or more compounds of formula I and/or pharmaceutically acceptable acid addition salts and, if desired, one or more other therapeutically valuable substances into a galenical administration form together with one or more therapeutically inert carriers.

In accordance with the invention compounds of formula I as well as their pharmaceutically acceptable salts are useful in the control or prevention of illnesses based on the adenosine receptor antagonistic activity, such as Alzheimer's disease, Parkinson's disease, neuroprotection, schizophrenia, anxiety, pain, respiration deficits, depression, asthma, allergic responses, hypoxia, ischaemia, seizure and substance abuse. Furthermore, compounds of the present invention may be useful as sedatives, muscle relaxants, antipsychotics, antiepileptics, anticonvulsants and cardiaprotective agents and for the production of corresponding medicaments.

The most preferred indications in accordance with the present invention are those, which include disorders of the central nervous system, for example the treatment or prevention of certain depressive disorders, neuroprotection and Parkinson's disease.

The dosage can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage may be administered as single dose or in divided doses and, in addition, the upper limit can also be exceeded when this is found to be indicated.

Unless stated to the contrary, all of the examples listed below were prepared and were characterized by the methods described above.

INTERMEDIATES

Example 1

8-Amino-2-thiophen-2-yl-[1,2,4]triazolo[1,5-a] pyridine-6-carboxylic Acid Methyl Ester a) 6-Hydroxy-5-nitro-nicotinic Acid To a solution of 30 g (0.217 mol) 6-hydroxy-nicotinic acid in 50 ml concentrated sulfuric acid was added 60 ml of a 1:1 mixture of conc. sulfuric acid and conc. nitric acid below 20° C. and stirred for 1 h at room temperature and afterwards heated to 80° C. for 4 h. The mixture was poured onto ice and the formed precipitate was collected and dried to yield 14.2 g (36%) of the title compound as a yellow amorphous solid.

MS m/e (%): 184 (MH$^+$, 100); 1H-NMR (300 MHz, DMSO-d6): δ=13.3 (s, br, 2H, COOH/OH), 8.65 (d, J=2.5 Hz, 1H, H-4), 8.38 (d, J=2.5 Hz, 1H, H-2).

b) 6-Amino-5-nitro-nicotinic Acid Methyl Ester

A mixture of 14.2 g (78 mmol) 6-hydroxy-5-nitro-nicotinic acid in 50 ml POCl$_3$ was heated to 130° C. for 5 h and afterwards the excess POCl$_3$ was distilled under reduced pressure. The residue was cooled to 0° C. and 150 ml methanol were slowly added. The mixture was stirred for 2 h at 0° C. After addition of 300 ml of a 25% NH$_3$ aq. solution the mixture was stirred for 4 h at room temperature. The precipitate was filtered washed once with diethyl ether and dried under vacuum to yield 5.97 g (39%) of the title compound as a yellow solid.

MS m/e (%): 197 (MH$^{30}$, 100); 1H-NMR (300 MHz, DMSO-d6): δ=8.83 (d, J=2.1 Hz, 1H, H-4), 8.72 (d, J=2.1 Hz, 1H, H-2), 8.38 (s, br, 2H, NH$_2$), 3.85 (s, 3H, OCH$_3$).

c) 5,6-Diamino-nicotinic Acid Methyl Ester

A suspension of 5.97 g (30 mmol) 6-amino-5-nitro-nicotinic acid methyl ester in 30 ml methanol and 600 mg Pd/C (10%) cat was added and hydrogenated at room temperature during 14 h. The catalyst was filtered off and the solution was concentrated to yield 4.74 g (94%) of the title compound as white amorphous solid.

MS m/e (%): 167 (MH$^{30}$, 100); 1H-NMR (300 MHz, DMSO-d6): δ=7.95 (d, J=1.5 Hz, 1H, H-4), 7.16 (d, J=1.5 Hz, 1H, H-2), 6.25 (s, br, 2H, NH$_2$), 4.91 (s, br, 2H, NH$_2$), 3.74 (s, 3H, OCH$_3$).

d) 8-Amino-2-thiophen-2-yl-[1,2,4]triazolo[1,5-a]pyridine-6-carboxylic Acid Methyl Ester A mixture of 1.114 g (6.66 mmol) 5,6-diamino-nicotinic acid methyl ester in 40 ml dioxane was treated with 1.578 g (7.33 mmol) O-mesitylenesulfonylhydroxylamine (prepared from ethyl-o-mesitylenesulfonylacetohydroxamate and HClO$_4$ (70%)) for 1 h at room temperature. 0.897 g (8 mmol) thiophene-2-carboxaldehyde and molecular sieves 4 Å was added and heated to 100° C. for 4 h before addition of 1.6 ml 5M KOH in methanol. The mixture was heated to 70° C. for 2 h and stirred at room temperature for 14 h. The volatiles were removed under reduced pressure and the residue was purified by flash column chromatography on silica eluting with a mixture of ethyl acetate and n-hexane to yield after evaporation 0.88 g (48%) of the title compound.

MS m/e (%): 275.3 (MH$^{30}$, 100); 1H-NMR (300 MHz, DMSO-d6): δ=8.65 (d, J 1.4 Hz, 1H, H-5), 7.81 (dd, J$_1$=3.5 Hz, J$_2$=1 Hz, 1H, thiophene H-2), 7.76 (dd, J$_1$=4.8 Hz, J$_2$=1 Hz, 1H, thiophene H-4), 7.24 (dd, J$_1$=4.8 Hz, J$_2$=3.5 Hz, 1H, thiophene H-3), 7.09 (d, J=1.4 Hz, 1H, H-7), 6.31 (s, br, 2H, NH$_2$), 3.88 (s, 3H, OCH$_3$).

Example 2

8-Amino-2-phenyl-[1,2,4]triazolo[1,5-a]pyridine-6-carboxylic Acid Methyl Ester

The title compound, MS m/e (%): 269 (M$^+$, 100), was prepared in accordance with the general method of example 1 from 5,6-diamino-nicotinic acid methyl ester, O-mesitylene-sulfonylhydroxylamine, and benzaldehyde. The purification was performed by flash column chromatography on silica eluting with a mixture of ethyl acetate and n-hexane.

Example 3

8-Amino-2-thiazol-2-yl-[1,2,4]triazolo[1,5-a]pyridine-6-carboxylic Acid Methyl Ester The title compound, MS m/e (%): 276.1 (M$^+$, 100), was prepared in accordance with the general method of example 1 from 5,6-diamino-nicotinic acid methyl ester, O-mesitylene-sulfonylhydroxylamine, and thiazole-2-carboxaldehyde. The purification was performed by flash column chromatography on silica eluting with a mixture of ethyl acetate and n-hexane.

Example 4

8-Amino-2-(5-methyl-thiophen-2-yl)-[1,2,4]triazolo[1,5-a]pyridine-6-carboxylic Acid Methyl Ester The title compound, MS m/e (%): 289.2 (M$^+$, 100), was prepared in accordance with the general method of example 1 from 5,6-diamino-nicotinic acid methyl ester, O-mesitylene-sulfonylhydroxylamine, and 5-methylthiophene-2-carboxaldehyde. The purification was performed by flash column chromatography on silica eluting with a mixture of ethyl acetate and n-hexane.

Example 5

8-Amino-2-furan-2-yl-[1,2,4]triazolo[1,5-a]pyridine-6-carboxylic Acid Methyl Ester The title compound, MS m/e (%): 259.1 (M$^+$, 100), was prepared in accordance with the general method of example 1 from 5,6-diamino-nicotinic acid methyl ester, O-mesitylene-sulfonylhydroxylamine, and furan-2-carboxaldehyde. The purification was performed by flash column chromatography on silica eluting with a mixture of ethyl acetate and n-hexane.

1H-NMR (300 MHz, DMSO-d6): δ=8.65 (d, J=1.5 Hz, 1H, H-5), 7.92 (dd, J$_1$=1.7 Hz, J$_2$=0.8 Hz, 1H, furan H-5), 7.16 (dd, J$_1$=3.4 Hz, J$_2$=0.8 Hz, 1H, furan H-3), 7.08 (d, J=1.5 Hz, 1H, H-7), 6.73 (dd, J$_1$=3.4 Hz, J$_2$=1.7 Hz, 1H, furan H-4), 6,35 (s, br, 2H, NH$_2$), 3.89 (s, 3H, OCH$_3$).

Example 6

8-Amino-2-(5-methyl-furan-2-yl)-[1,2,4]triazolo[1,5-a]pyridine-6-carboxylic Acid Methyl Ester The title compound, MS m/e (%): 273.2 (M$^+$, 100), was prepared in accordance with the general method of example 1 from 5,6-diamino-nicotinic acid methyl ester, O-mesitylene-sulfonylhydroxylamine, and 5-methylfuran-2-carboxaldehyde. The purification was performed by flash column chromatography on silica eluting with a mixture of ethyl acetate and n-hexane.

Example 7

8-Amino-2-(5-bromo-furan-2-yl)-[1,2,4]triazolo[1,5-a]pyridine-6-carboxylic Acid Methyl Ester The title compound, MS m/e (%): 338.2 (M$^+$, 100), was prepared in accordance with the general method of example 1 from 5,6-diamino-nicotinic acid methyl ester, O-mesitylene-sulfonylhydroxylamine, and 5-bromofuran-2-carboxaldehyde. The purification was performed by flash column chromatography on silica eluting with a mixture of ethyl acetate and n-hexane.

Example 8

8-Amino-2-pyridin-2-yl-[1,2,4]triazolo[1,5-a]pyridine-6-carboxylic Acid Methyl Ester The title compound, MS m/e (%): 270.3 (M$^+$, 100), was prepared in accordance with the general method of example 1 from 5,6-Diamino-nicotinic acid methyl ester, O-mesitylene-sulfonylhydroxylamine, and pyridine-2-carboxaldehyde. The purification was performed by flash column chromatography on silica eluting with a mixture of ethyl acetate and n-hexane.

1H-NMR (300 MHz, DMSO-d6): δ=8.75 (dd, J$_1$=2 Hz, J$_2$=0.6 Hz, 1H, pyridine H-6), 8.70 (d, J=1.5 Hz, 1H, H-5), 8.25 (dd, J$_1$=7.8 Hz, J$_2$=0.6 Hz, 1H, pyridine H-3), 8.00 (dd, J$_1$=7.8 Hz, J$_2$=2 Hz, 1H, pyridine H-4), 7.54 (dd, J$_1$=7.8 Hz, J$_2$=1.2 Hz, 1H, pyridine H-5), 7.09 (d, J=1.5 Hz, 1H, H-7), 6.41 (s, br, 2H, NH$_2$), 3.89 (s, 3H, OCH$_3$).

PHARMACEUTICALLY ACTIVE COMPOUNDS

Example 9

[8-Amino-2-(5-bromo-furan-2-yl)-[1,2,4]triazolo[1,5-a]pyridin-6-yl]-piperidin-1-yl-methanone A solution of 20 mg (0.24 mmol) piperidine in 1 ml dioxane was treated with 0.24 ml (0.24 mmol) trimethylaluminum in toluene and stirred for 1 h at room temperature. 20 mg (0.06 mmol) 8-Amino-2-(5-bromo-furan-2-yl)-[1,2,4]triazolo[1,5-a]pyridine-6-carboxylic acid methyl ester in 1 ml dioxane was added and the mixture was heated to 90° C. for 72 h. 0.5 ml 1N HCl aq. was added and the volatiles were removed. The residue was taken up in 1.5 ml formic acid and 0.5 ml methanol and purified by reversed phase preparative HPLC eluting with a gradient of acetonitrile and water. The elution solvents were evaporated to obtain 7 mg (29%) of the title compound.

MS m/e (%): 391.3 (MH$^{30}$, 100); 1H-NMR (500 MHz, DMSO): δ=8.21 (s, 1H, H-5), 7.14 (dd, J$_1$=3.5 Hz, 1H, furan H-4), 6.82 (d, J=3.5 Hz, 1H, furan H-3), 6.56 (s, 1H, H-7), 6.26 (s, br, 2H, NH$_2$), 1.62 (m, 4H, NCH$_2$), 1.52 (m, 6H, CH2).

According to example 9 further [1,2,4]triazolo[1,5-a]pyridin-6-carboxamide derivatives have been synthesized from the esters described in example 1–8 and the respective amine. The results are compiled in the following list comprising examples 10 to example 108.

| Ex. No. | hA2a $K_i$ (nM) | hA1 $K_i$ (nM) | Select. A1/A2a | Structure | Name | MW | MS m/e (%) |
|---|---|---|---|---|---|---|---|
| 10 | 277.2 | 2256.2 | 8.1 | 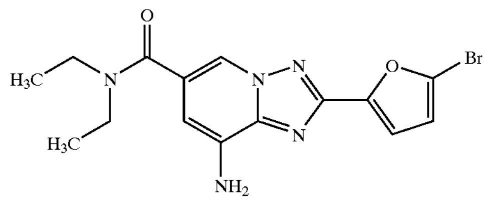 | 8-Amino-2-(5-bromo-furan-2-yl)-[1,2,4]triazolo[1,5-a]pyridine-6-carboxylic acid diethylamide | 378.2 | MH+ (100) |
| 11 | 35.2 | 1273.3 | 36.2 | 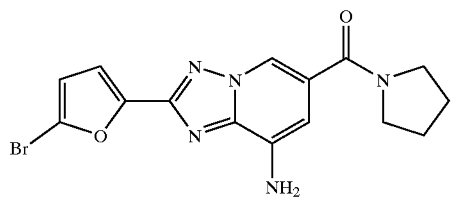 | [8-Amino-2-(5-bromo-furan-2-yl)-[1,2,4]triazolo[1,5-a]pyridin-6-yl]-pyrrolidin-1-yl-methanone | 376.2 | MH+ (100) |
| 12 | 26.8 | 1120 | 41.8 | 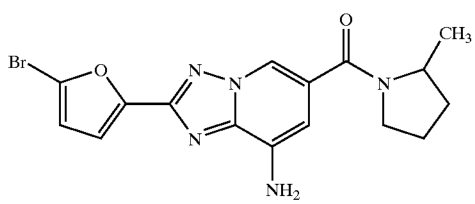 | [8-Amino-2-(5-bromo-furan-2-yl)-[1,2,4]triazolo[1,5-a]pyridin-6-yl]-(2-methyl-pyrrolidin-1-yl)-methanone | 390.2 | MH+ (100) |
| 13 | 40.5 | 2686.7 | 66.3 | 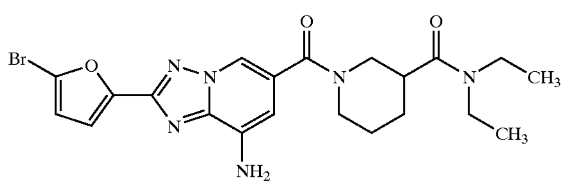 | 1-[8-Amino-2-(5-bromo-furan-2-yl)-[1,2,4]triazolo[1,5-a]pyridine-6-carbonyl]-piperidine-3-carboxylic acid diethylamide | 489.4 | MH+ (100) |
| 14 | 37.2 | 1191.7 | 32 | 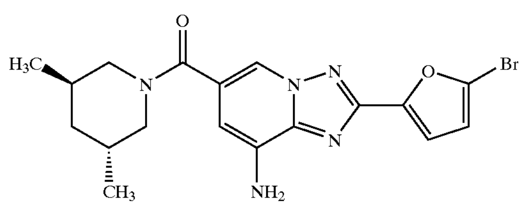 | [8-Amino-2-(5-bromo-furan-2-yl)-[1,2,4]triazolo[1,5-a]pyridin-6-yl]-(3,5-dimethyl-piperidin-1-yl)-methanone | 418.3 | MH+ (100) |
| 15 | 62.4 | 1943.3 | 31.1 | 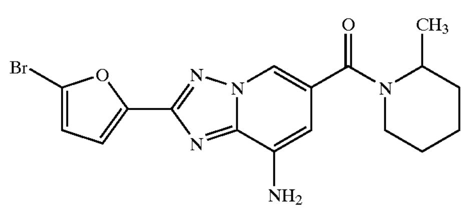 | [8-Amino-2-(5-bromo-furan-2-yl)-[1,2,4]triazolo[1,5-a]pyridin-6-yl]-(2-methyl-piperidin-1-yl)-methanone | 404.3 | MH+ (100) |
| 16 | 16.4 | 1053.3 | 64.2 | 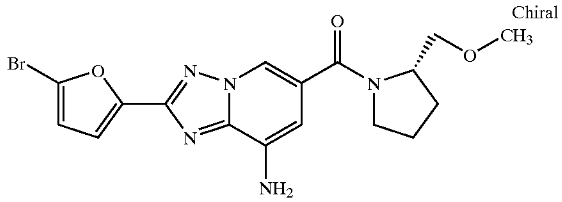 | [8-Amino-2-(5-bromo-furan-2-yl)-[1,2,4]triazolo[1,5-a]pyridin-6-yl]-(2-methoxymethyl-pyrrolidin-1-yl)-methanone | 420.3 | MH+ (100) |

-continued

| Ex. No. | hA2a K_i (nM) | hA1 K_i (nM) | Select. A1/A2a | Structure | Name | MW | MS m/e (%) |
|---|---|---|---|---|---|---|---|
| 17 | 61.2 | 1233.3 | 20.2 | 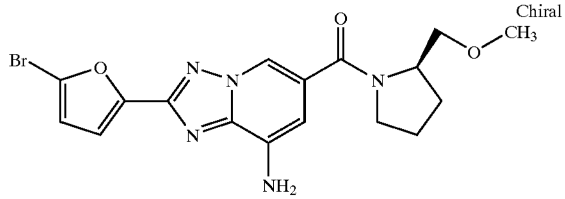 | [8-Amino-2-(5-bromo-furan-2-yl)-[1,2,4]triazolo[1,5-a]pyridin-6-yl]-((S)-2-methoxymethyl-pyrrolidin-1-yl)-methanone | 420.3 | MH+ (100) |
| 18 | 67 | 1106.7 | 16.5 | 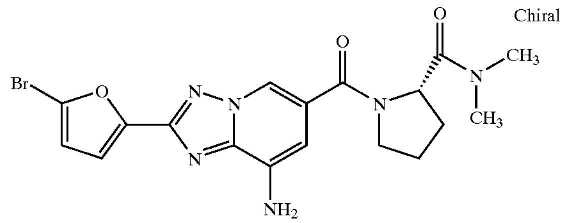 | 1-[8-Amino-2-(5-bromo-furan-2-yl)-[1,2,4]triazolo[1,5-a]pyridine-6-carbonyl]-pyrrolidine-2-carboxylic acid (S)-dimethylamide | 447.3 | MH+ (100) |
| 19 | 23.2 | 2996.7 | 129.2 | 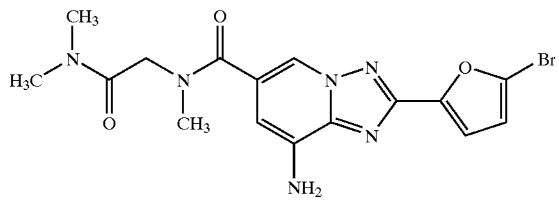 | 8-Amino-2-(5-bromo-furan-2-yl)-[1,2,4]triazolo[1,5-a]pyridine-6-carboxylic acid dimethylcarbamoyl-methyl-methyl-amide | 421.3 | MH+ (100) |
| 20 | 15.5 | 803.3 | 51.8 | 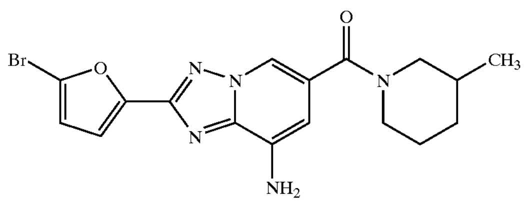 | [8-Amino-2-(5-bromo-furan-2-yl)-[1,2,4]triazolo[1,5-a]pyridin-6-yl]-(3-methyl-piperidin-1-yl)-methanone | 404.3 | MH+ (100) |
| 21 | 44.6 | 1153.3 | 25.9 | 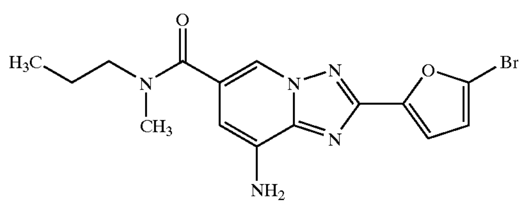 | 8-Amino-2-(5-bromo-furan-2-yl)-[1,2,4]triazolo[1,5-a]pyridine-6-carboxylic acid methyl-propyl-amide | 378.2 | MH+ (100) |
| 22 | 76.2 | 1416.7 | 18.6 | 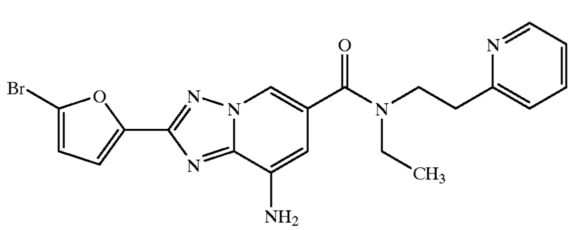 | 8-Amino-2-(5-bromo-furan-2-yl)-[1,2,4]triazolo[1,5-a]pyridine-6-carboxylic acid ethyl-(2-pyridin-2-yl-ethyl)-amide | 455.3 | MH+ (100) |
| 23 | 73 | 936.7 | 12.8 | 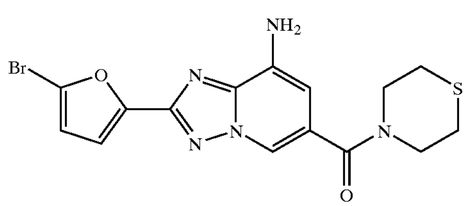 | [8-Amino-2-(5-bromo-furan-2-yl)-[1,2,4]triazolo[1,5-a]pyridin-6-yl]-thiomorpholin-4-yl-methanone | 408.3 | MH+ (100) |

-continued

| Ex. No. | hA2a K$_i$ (nM) | hA1 K$_i$ (nM) | Select. A1/A2a | Structure | Name | MW | MS m/e (%) |
|---|---|---|---|---|---|---|---|
| 24 | 110.8 | 830 | 7.5 | 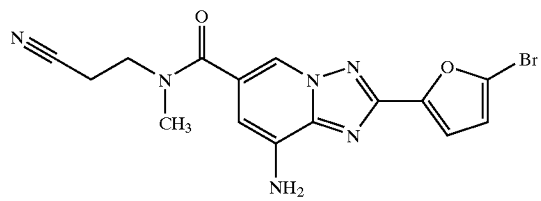 | 8-Amino-2-(5-bromo-furan-2-yl)-[1,2,4]triazolo[1,5-a]pyridine-6-carboxylic acid (2-cyano-ethyl)-methyl-amide | 389.2 | MH$^+$ (100) |
| 25 | 50 | 589.7 | 11.8 | 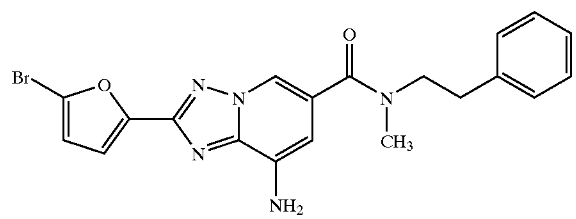 | 8-Amino-2-(5-bromo-furan-2-yl)-[1,2,4]triazolo[1,5-a]pyridine-6-carboxylic acid methyl-phenethyl-amide | 440.3 | MH$^+$ (100) |
| 26 | 192.2 | 3570 | 18.6 | 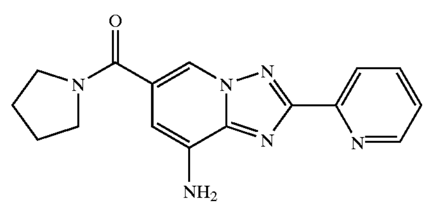 | (8-Amino-2-pyridin-2-yl-[1,2,4]triazolo[1,5-a]pyridin-6-yl)-pyrrolidin-1-yl-methanone | 308.3 | MH$^+$ (100) |
| 27 | 548 | | | 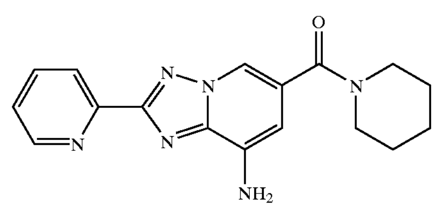 | (8-Amino-2-pyridin-2-yl-[1,2,4]triazolo[1,5-a]pyridin-6-yl)-piperidin-1-yl-methanone | 322.4 | MH$^+$ (100) |
| 28 | 369.2 | | | 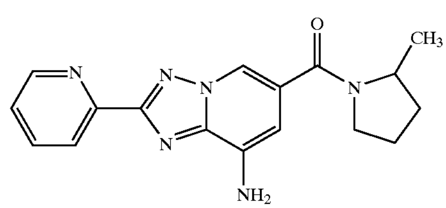 | (8-Amino-2-pyridin-2-yl-[1,2,4]triazolo[1,5-a]pyridin-6-yl)-(2-methyl-pyrrolidin-1-yl)-methanone | 322.4 | MH$^+$ (100) |
| 29 | 594 | | | 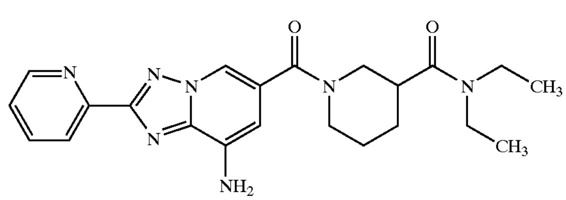 | 1-(8-Amino-2-pyridin-2-yl-[1,2,4]triazolo[1,5-a]pyridine-6-carbonyl)-piperidine-3-carboxylic acid diethylamide | 421.5 | MH$^+$ (100) |
| 30 | 578 | | | 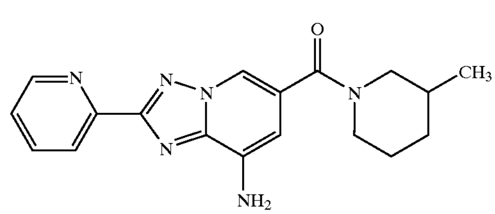 | (8-Amino-2-pyridin-2-yl-[1,2,4]triazolo[1,5-a]pyridin-6-yl)-(3-methyl-piperidin-1-yl)-methanone | 336.4 | MH$^+$ (100) |

-continued

| Ex. No. | hA2a K$_i$ (nM) | hA1 K$_i$ (nM) | Select. A1/A2a | Structure | Name | MW | MS m/e (%) |
|---|---|---|---|---|---|---|---|
| 31 | 796 | | | 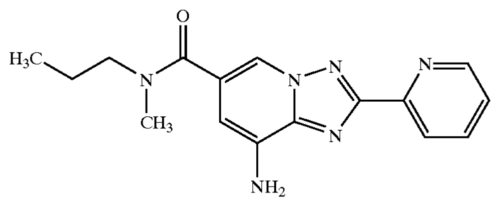 | 8-Amino-2-pyridin-2-yl-[1,2,4]triazolo[1,5-a]pyridine-6-carboxylic acid methyl-propyl-amide | 310.4 | MH$^+$ (100) |
| 32 | 386.8 | | | 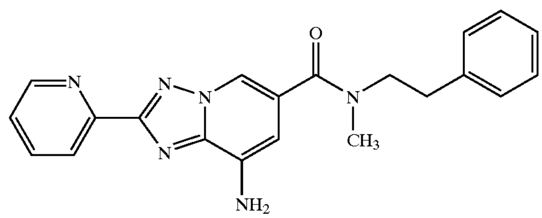 | 8-Amino-2-pyridin-2-yl-[1,2,4]triazolo[1,5-a]pyridine-6-carboxylic acid methyl-phenethyl-amide | 372.4 | MH$^+$ (100) |
| 33 | 422 | | | 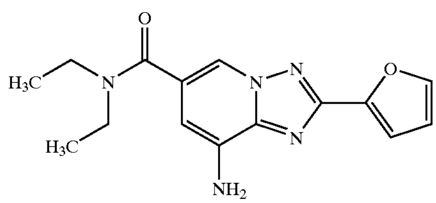 | 8-Amino-2-furan-2-yl-[1,2,4]triazolo[1,5-a]pyridine-6-carboxylic acid diethylamide | 299.3 | MH$^+$ (100) |
| 34 | 56.8 | 4196.7 | 73.9 | 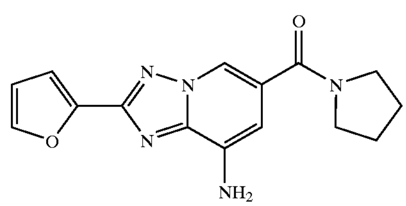 | (8-Amino-2-furan-2-yl-[1,2,4]triazolo[1,5-a]pyridin-6-yl)-pyrrolidin-1-yl-methanone | 297.3 | MH$^+$ (100) |
| 35 | 190.4 | 3443.3 | 18.1 | 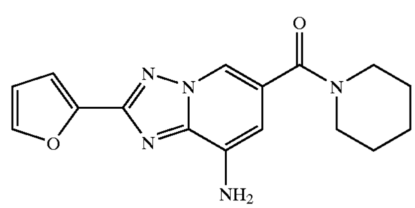 | (8-Amino-2-furan-2-yl-[1,2,4]triazolo[1,5-a]pyridin-6-yl)-piperidin-1-yl-methanone | 311.3 | MH$^+$ (100) |
| 36 | 228.6 | | | 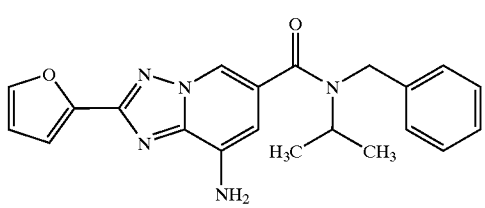 | 8-Amino-2-furan-2-yl-[1,2,4]triazolo[1,5-a]pyridine-6-carboxylic acid benzyl-isopropyl-amide | 375.4 | MH$^+$ (100) |
| 37 | 34.9 | 2940 | 84.2 | 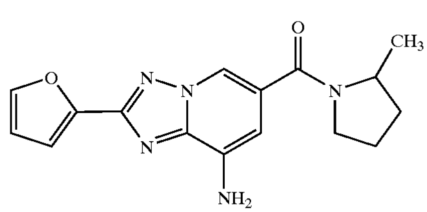 | (8-Amino-2-furan-2-yl-[1,2,4]triazolo[1,5-a]pyridin-6-yl)-(2-methyl-pyrrolidin-1-yl)-methanone | 311.3 | MH$^+$ (100) |

-continued

| Ex. No. | hA2a K$_i$ (nM) | hA1 K$_i$ (nM) | Select. A1/A2a | Structure | Name | MW | MS m/e (%) |
|---|---|---|---|---|---|---|---|
| 38 | 369.8 | | | 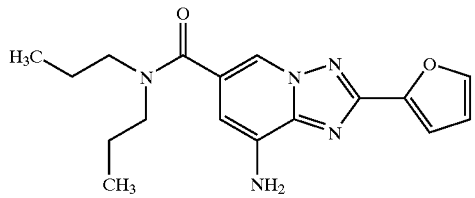 | 8-Amino-2-furan-2-yl-[1,2,4]triazolo[1,5-a]pyridine-6-carboxylic acid dipropylamide | 327.4 | MH$^+$ (100) |
| 39 | 136.2 | 2186.7 | 16.1 | 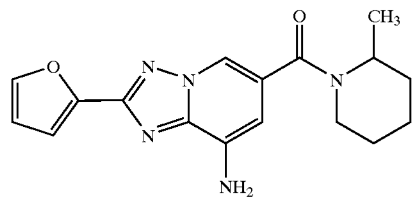 | (8-Amino-2-furan-2-yl-[1,2,4]triazolo[1,5-a]pyridin-6-yl)-(2-methyl-piperidin-1-yl)-methanone | 325.4 | MH$^+$ (100) |
| 40 | 371.4 | | | 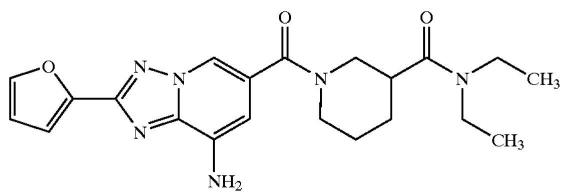 | 1-(8-Amino-2-furan-2-yl-[1,2,4]triazolo[1,5-a]pyridine-6-carbonyl)-piperidine-3-carboxylic acid diethylamide | 410.5 | MH$^+$ (100) |
| 41 | 77.6 | 4360 | 56.2 | 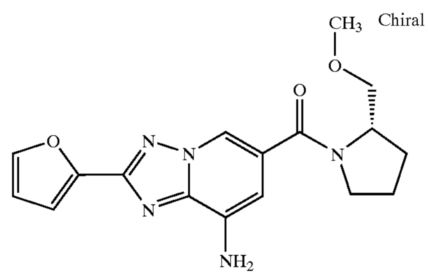 | (8-Amino-2-furan-2-yl-[1,2,4]triazolo[1,5-a]pyridin-6-yl)-(2-R-methoxymethyl-pyrrolidin-1-yl)-methanone | 341.4 | MH$^+$ (100) |
| 42 | 69.4 | 5626.7 | 81.1 | 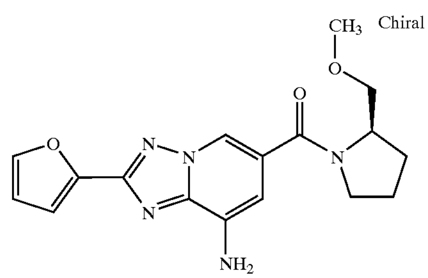 | (8-Amino-2-furan-2-yl-[1,2,4]triazolo[1,5-a]pyridin-6-yl)-(2-S-methoxymethyl-pyrrolidin-1-yl)-methanone | 341.4 | MH$^+$ (100) |
| 43 | 138.4 | 2333.3 | 16.9 | 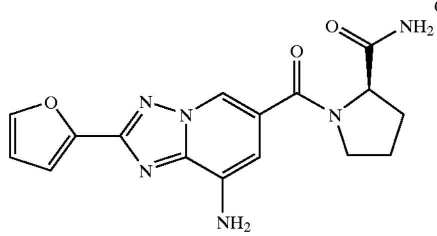 | 1-(8-Amino-2-furan-2-yl-[1,2,4]triazolo[1,5-a]pyridine-6-carbonyl)-pyrrolidine-2-R-carboxylic acid amide | 340.3 | MH$^+$ (100) |

-continued

| Ex. No. | hA2a $K_i$ (nM) | hA1 $K_i$ (nM) | Select. A1/A2a | Structure | Name | MW | MS m/e (%) |
|---|---|---|---|---|---|---|---|
| 44 | 342.6 | | | 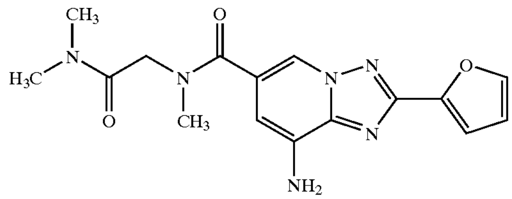 | 8-Amino-2-furan-2-yl-[1,2,4]triazolo[1,5-a]pyridine-6-carboxylic acid dimethylcarbamoyl-methyl-methyl-amide | 342.4 | MH+ (100) |
| 45 | 506 | | | 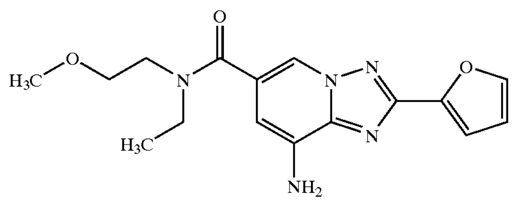 | 8-Amino-2-furan-2-yl-[1,2,4]triazolo[1,5-a]pyridine-6-carboxylic acid ethyl-(2-methoxy-ethyl)-amide | 329.4 | MH+ (100) |
| 46 | 131.4 | 2686.7 | 20.4 | 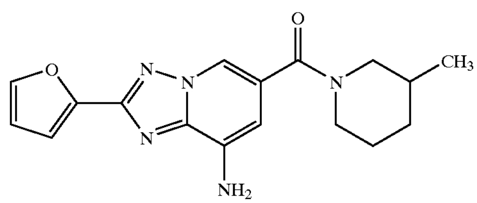 | (8-Amino-2-furan-2-yl-[1,2,4]triazolo[1,5-a]pyridin-6-yl)-(3-methyl-piperidin-1-yl)-methanone | 325.4 | MH+ (100) |
| 47 | 240.6 | | | 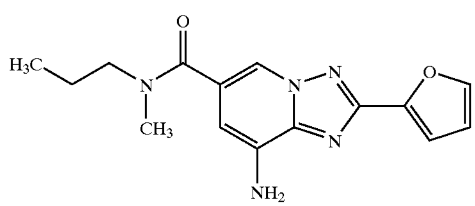 | 8-Amino-2-furan-2-yl-[1,2,4]triazolo[1,5-a]pyridine-6-carboxylic acid methyl-propyl-amide | 299.3 | MH+ (100) |
| 48 | 32.7 | 246.7 | 7.5 | 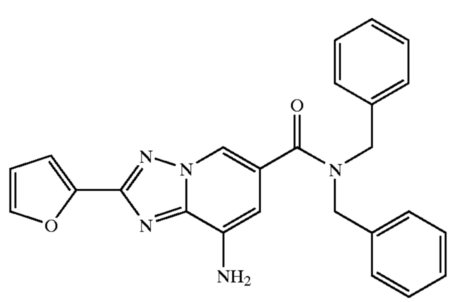 | 8-Amino-2-furan-2-yl-[1,2,4]triazolo[1,5-a]pyridine-6-carboxylic acid dibenzylamide | 423.5 | MH+ (100) |
| 49 | 638 | | | 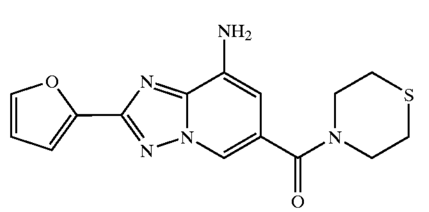 | (8-Amino-2-furan-2-yl-[1,2,4]triazolo[1,5-a]pyridin-6-yl)-thiomorpholin-4-yl-methanone | 329.4 | MH+ (100) |
| 50 | 251.2 | | | 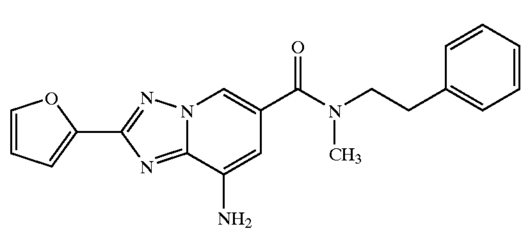 | 8-Amino-2-furan-2-yl-[1,2,4]triazolo[1,5-a]pyridine-6-carboxylic acid methyl-phenethyl-amide | 361.4 | MH+ (100) |

| Ex. No. | hA2a K$_i$ (nM) | hA1 K$_i$ (nM) | Select. A1/A2a | Structure | Name | MW | MS m/e (%) |
|---|---|---|---|---|---|---|---|
| 51 | 196.8 | 724.7 | 3.7 | 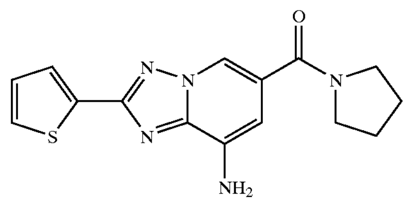 | (8-Amino-2-thiophen-2-yl-[1,2,4]triazolo[1,5-a]pyridin-6-yl)-pyrrolidin-1-yl-methanone | 313.4 | MH$^+$ (100) |
| 52 | 353.2 | | | 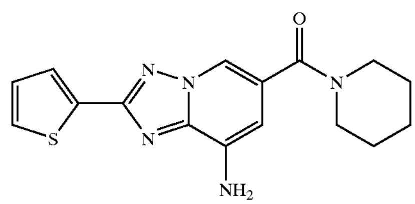 | (8-Amino-2-thiophen-2-yl-[1,2,4]triazolo[1,5-a]pyridin-6-yl)-piperidin-1-yl-methanone | 327.4 | MH$^+$ (100) |
| 53 | 232.8 | | | 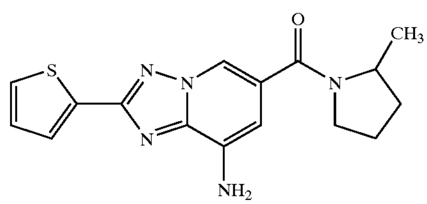 | (8-Amino-2-thiophen-2-yl-[1,2,4]triazolo[1,5-a]pyridin-6-yl)-(2-methyl-pyrrolidin-1-yl)-methanone | 327.4 | MH$^+$ (100) |
| 54 | 552 | | | 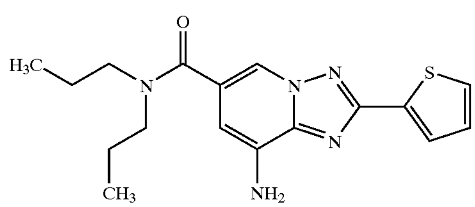 | 8-Amino-2-thiophen-2-yl-[1,2,4]triazolo[1,5-a]pyridine-6-carboxylic acid dipropylamide | 343.5 | MH$^+$ (100) |
| 55 | 260 | | | 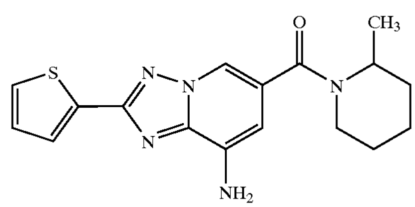 | (8-Amino-2-thiophen-2-yl-[1,2,4]triazolo[1,5-a]pyridin-6-yl)-(2-methyl-piperidin-1-yl)-methanone | 341.4 | MH$^+$ (100) |
| 56 | 684 | | | 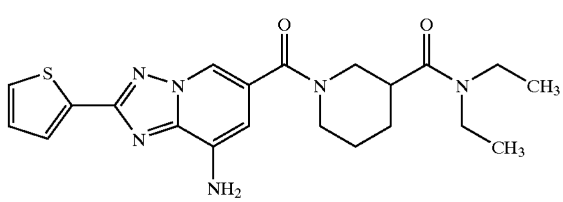 | 1-(8-Amino-2-thiophen-2-yl-[1,2,4]triazolo[1,5-a]pyridine-6-carbonyl)-piperidine-3-carboxylic acid diethylamide | 426.5 | MH$^+$ (100) |
| 57 | 242.2 | | | 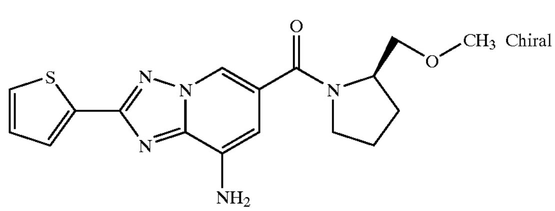 | (8-Amino-2-thiophen-2-yl-[1,2,4]triazolo[1,5-a]pyridin-6-yl)-(2-R-methoxymethyl-pyrrolidin-1-yl)-methanone | 357.4 | MH$^+$ (100) |

| Ex. No. | hA2a K_i (nM) | hA1 K_i (nM) | Select. A1/A2a | Structure | Name | MW | MS m/e (%) |
|---|---|---|---|---|---|---|---|
| 58 | 892 | | | 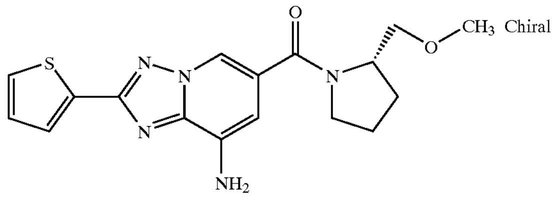 | (8-Amino-2-thiophen-2-yl-[1,2,4]triazolo[1,5-a]pyridin-6-yl)-(2-S-methoxymethyl-pyrrolidin-1-yl)-methanone | 357.4 | MH+ (100) |
| 59 | 214.6 | | | 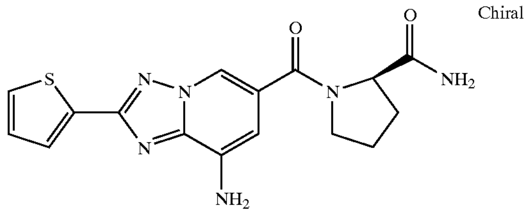 | 1-(8-Amino-2-thiophen-2-yl-[1,2,4]triazolo[1,5-a]pyridine-6-carbonyl)-pyrrolidine-2-R-carboxylic acid amide | 356.4 | MH+ (100) |
| 60 | 548 | | | 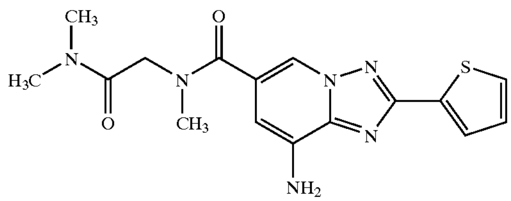 | 8-Amino-2-thiophen-2-yl-[1,2,4]triazolo[1,5-a]pyridine-6-carboxylic acid dimethylcarbamoyl-methyl-methyl-amide | 358.4 | MH+ (100) |
| 61 | 920 | | | 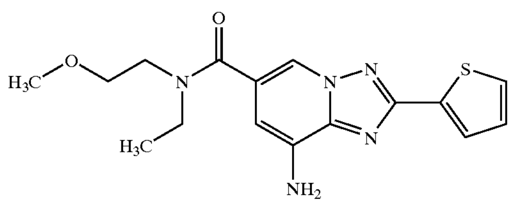 | 8-Amino-2-thiophen-2-yl-[1,2,4]triazolo[1,5-a]pyridine-6-carboxylic acid ethyl-(2-methoxy-ethyl)-amide | 345.4 | MH+ (100) |
| 62 | 716 | | | 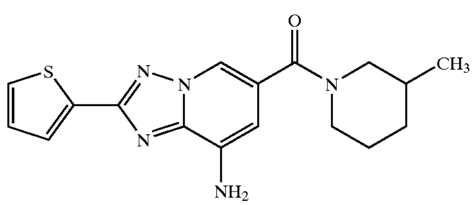 | (8-Amino-2-thiophen-2-yl-[1,2,4]triazolo[1,5-a]pyridin-6-yl)-(3-methyl-piperidin-1-yl)-methanone | 341.4 | MH+ (100) |
| 63 | 440 | | | 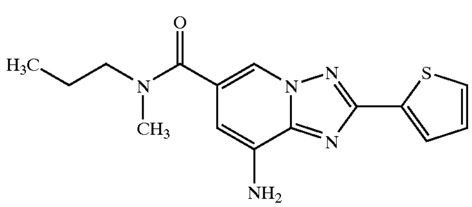 | 8-Amino-2-thiophen-2-yl-[1,2,4]triazolo[1,5-a]pyridine-6-carboxylic acid methyl-propyl-amide | 315.4 | MH+ (100) |
| 64 | 83 | 310.7 | 3.7 | 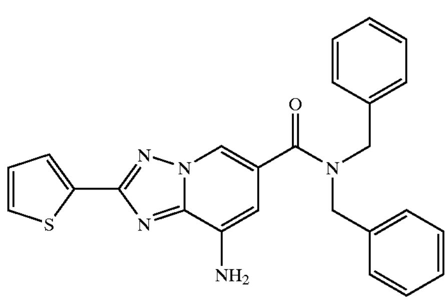 | 8-Amino-2-thiophen-2-yl-[1,2,4]triazolo[1,5-a]pyridine-6-carboxylic acid dibenzylamide | 439.5 | MH+ (100) |

| Ex. No. | hA2a K<sub>i</sub> (nM) | hA1 K<sub>i</sub> (nM) | Select. A1/A2a | Structure | Name | MW | MS m/e (%) |
|---|---|---|---|---|---|---|---|
| 65 | 718 | | | 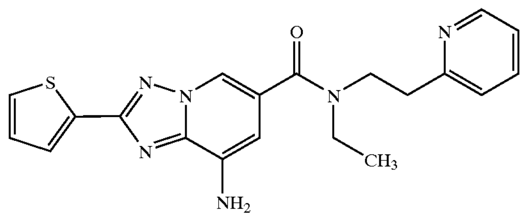 | 8-Amino-2-thiophen-2-yl-[1,2,4]triazolo[1,5-a]pyridine-6-carboxylic acid ethyl-(2-pyridin-2-yl-ethyl)-amide | 392.5 | MH+ (100) |
| 66 | 982 | | | 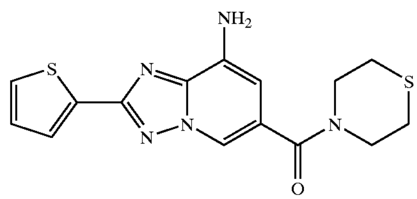 | (8-Amino-2-thiophen-2-yl-[1,2,4]triazolo[1,5-a]pyridin-6-yl)-thiomorpholin-4-yl-methanone | 345.4 | MH+ (100) |
| 67 | 395.2 | | | 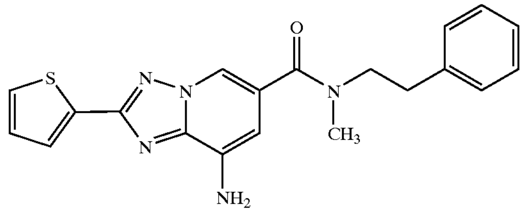 | 8-Amino-2-thiophen-2-yl-[1,2,4]triazolo[1,5-a]pyridine-6-carboxylic acid methyl-phenethyl-amide | 377.5 | MH+ (100) |
| 68 | 246.2 | | | 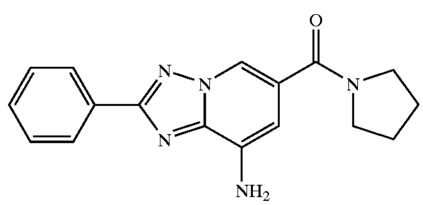 | (8-Amino-2-phenyl-[1,2,4]triazolo[1,5-a]pyridin-6-yl)-pyrrolidin-1-yl-methanone | 307.4 | MH+ (100) |
| 69 | 554 | | | 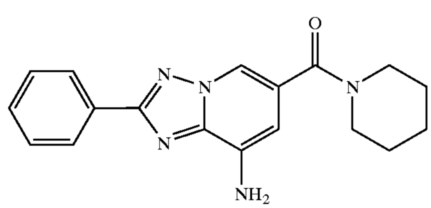 | (8-Amino-2-phenyl-[1,2,4]triazolo[1,5-a]pyridin-6-yl)-piperidin-1-yl-methanone | 321.4 | MH+ (100) |
| 70 | 144.6 | | | 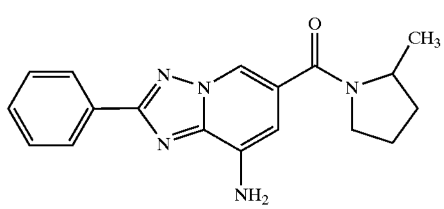 | (8-Amino-2-phenyl-[1,2,4]triazolo[1,5-a]pyridin-6-yl)-(2-methyl-pyrrolidin-1-yl)-methanone | 321.4 | MH+ (100) |
| 71 | 484 | | | 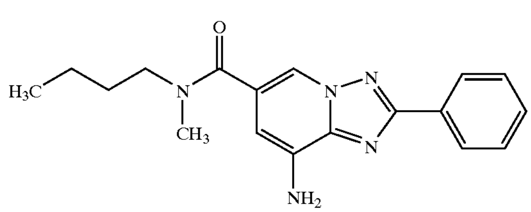 | 8-Amino-2-phenyl-[1,2,4]triazolo[1,5-a]pyridine-6-carboxylic acid methyl-butyl-amide | 323.4 | MH+ (100) |

| Ex. No. | hA2a $K_i$ (nM) | hA1 $K_i$ (nM) | Select. A1/A2a | Structure | Name | MW | MS m/e (%) |
|---|---|---|---|---|---|---|---|
| 72 | 361 | | | 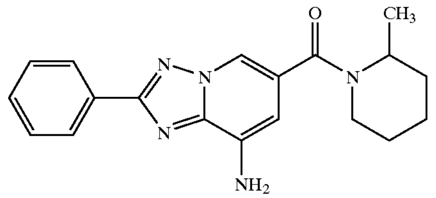 | (8-Amino-2-phenyl-[1,2,4]triazolo[1,5-a]pyridin-6-yl)-(2-methyl-piperidin-1-yl)-methanone | 335.4 | MH⁺ (100) |
| 73 | 998 | | | 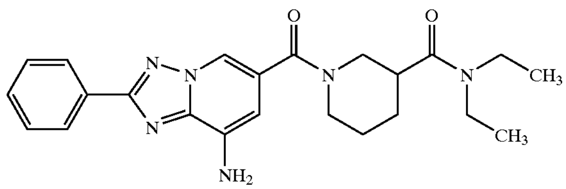 | 1-(8-Amino-2-phenyl-[1,2,4]triazolo[1,5-a]pyridine-6-carbonyl)-piperidine-3-carboxylic acid diethylamide | 420.5 | MH⁺ (100) |
| 74 | 196 | | | Chiral | (8-Amino-2-phenyl-[1,2,4]triazolo[1,5-a]pyridin-6-yl)-(2-methoxymethyl-pyrrolidin-1-yl)-methanone | 351.4 | MH⁺ (100) |
| 75 | 413 | | | Chiral | (8-Amino-2-phenyl-[1,2,4]triazolo[1,5-a]pyridin-6-yl)-((S)-2-methoxymethyl-pyrrolidin-1-yl)-methanone | 351.4 | MH⁺ (100) |
| 76 | 420.2 | | | Chiral | 1-(8-Amino-2-phenyl-[1,2,4]triazolo[1,5-a]pyridine-6-carbonyl)-pyrrolidine-2-carboxylic acid dimethylamide | 378.4 | MH⁺ (100) |
| 77 | 674 | | | 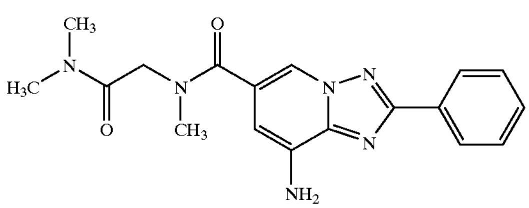 | 8-Amino-2-phenyl-[1,2,4]triazolo[1,5-a]pyridine-6-carboxylic acid dimethylcarbamoyl-methyl-methyl-amide | 352.4 | MH⁺ (100) |
| 78 | 384.6 | | | 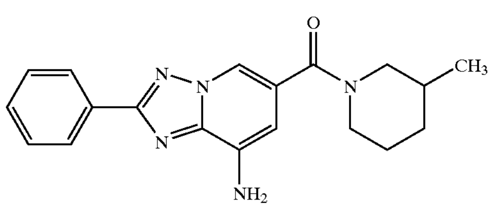 | (8-Amino-2-phenyl-[1,2,4]triazolo[1,5-a]pyridin-6-yl)-(3-methyl-piperidin-1-yl)-methanone | 335.4 | MH⁺ (100) |

-continued

| Ex. No. | hA2a $K_i$ (nM) | hA1 $K_i$ (nM) | Select. A1/A2a | Structure | Name | MW | MS m/e (%) |
|---|---|---|---|---|---|---|---|
| 79 | 886 | | | 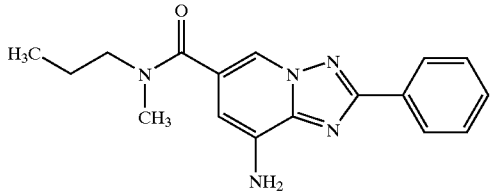 | 8-Amino-2-phenyl-[1,2,4]triazolo[1,5-a]pyridine-6-carboxylic acid methyl-propyl-amide | 309.4 | MH+ (100) |
| 80 | 289 | | | 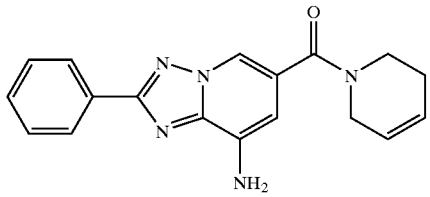 | (8-Amino-2-phenyl-[1,2,4]triazolo[1,5-a]pyridin-6-yl)-(3,6-dihydro-2H-pyridin-1-yl)-methanone | 319.4 | MH+ (100) |
| 81 | 524 | | | 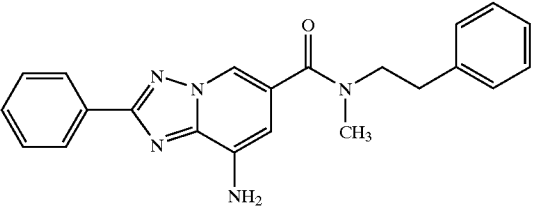 | 8-Amino-2-phenyl-[1,2,4]triazolo[1,5-a]pyridine-6-carboxylic acid methyl-phenethyl-amide | 371.4 | MH+ (100) |
| 82 | 131.4 | | | 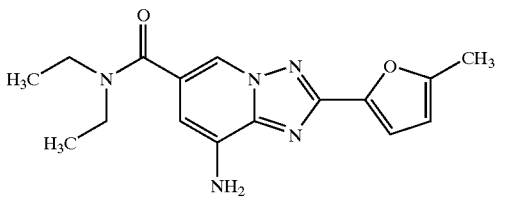 | 8-Amino-2-(5-methyl-furan-2-yl)-[1,2,4]triazolo[1,5-a]pyridine-6-carboxylic acid diethylamide | 313.4 | MH+ (100) |
| 83 | 75.6 | 1640 | 21.7 | 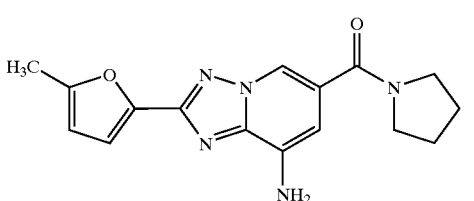 | [8-Amino-2-(5-methyl-furan-2-yl)-[1,2,4]triazolo[1,5-a]pyridin-6-yl]-pyrrolidin-1-yl-methanone | 311.3 | MH+ (100) |
| 84 | 56.8 | 1273.3 | 22.4 | 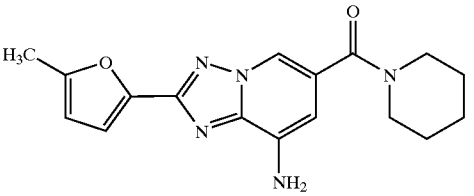 | [8-Amino-2-(5-methyl-furan-2-yl)-[1,2,4]triazolo[1,5-a]pyridin-6-yl]-piperidin-1-yl-methanone | 325.4 | MH+ (100) |
| 85 | 75.2 | 1360 | 18.1 | 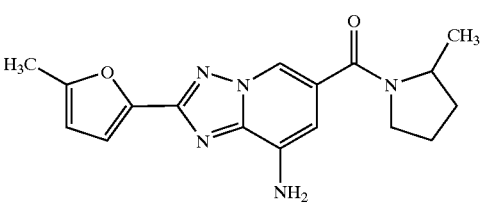 | [8-Amino-2-(5-methyl-furan-2-yl)-[1,2,4]triazolo[1,5-a]pyridin-6-yl]-(2-methyl-pyrrolidin-1-yl)-methanone | 325.4 | MH+ (100) |

-continued

| Ex. No. | hA2a K$_i$ (nM) | hA1 K$_i$ (nM) | Select. A1/A2a | Structure | Name | MW | MS m/e (%) |
|---|---|---|---|---|---|---|---|
| 86 | 230 | | | 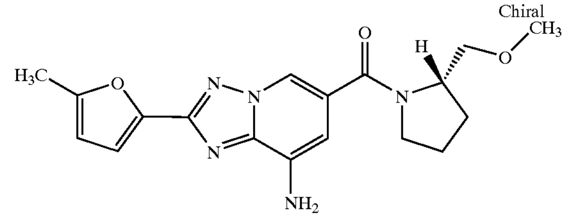 | [8-Amino-2-(5-methyl-furan-2-yl)-[1,2,4]triazolo[1,5-a]pyridin-6-yl]-(2-methoxymethyl-pyrrolidin-1-yl)-methanone | 355.4 | MH$^+$ (100) |
| 87 | 104.4 | | | 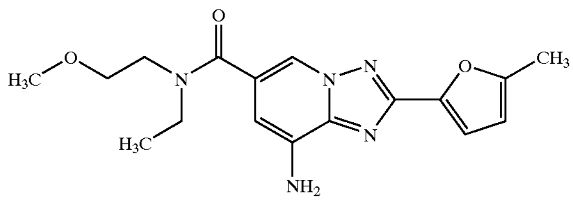 | 8-Amino-2-(5-methyl-furan-2-yl)-[1,2,4]triazolo[1,5-a]pyridine-6-carboxylic acid ethyl-(2-methoxy-ethyl)-amide | 343.4 | MH$^+$ (100) |
| 88 | 56.2 | 1350 | 24 | 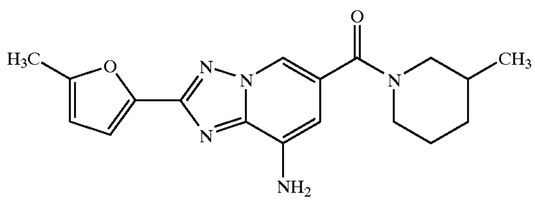 | [8-Amino-2-(5-methyl-furan-2-yl)-[1,2,4]triazolo[1,5-a]pyridin-6-yl]-(3-methyl-piperidin-1-yl)-methanone | 339.4 | MH$^+$ (100) |
| 89 | 177.6 | | | 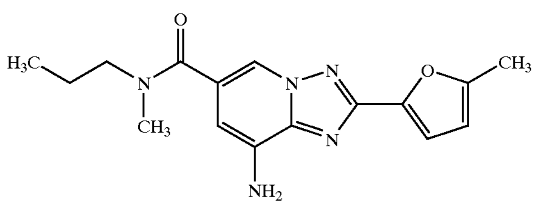 | 8-Amino-2-(5-methyl-furan-2-yl)-[1,2,4]triazolo[1,5-a]pyridine-6-carboxylic acid methyl-propyl-amide | 313.4 | MH$^+$ (100) |
| 90 | 139.8 | | | 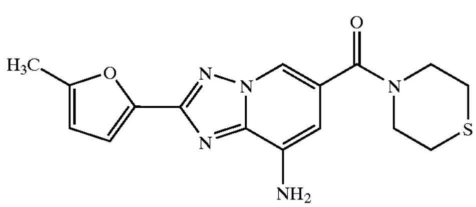 | [8-Amino-2-(5-methyl-furan-2-yl)-[1,2,4]triazolo[1,5-a]pyridin-6-yl]-thiomorpholin-4-yl-methanone | 343.4 | MH$^+$ (100) |
| 91 | 111.6 | | | 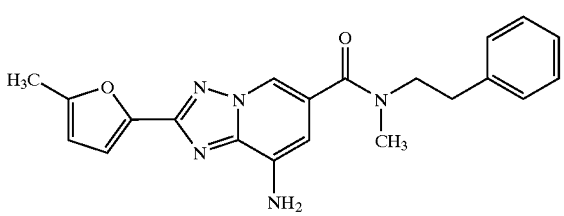 | 8-Amino-2-(5-methyl-furan-2-yl)-[1,2,4]triazolo[1,5-a]pyridine-6-carboxylic acid methyl-phenethyl-amide | 375.4 | MH$^+$ (100) |
| 92 | 249.4 | | | 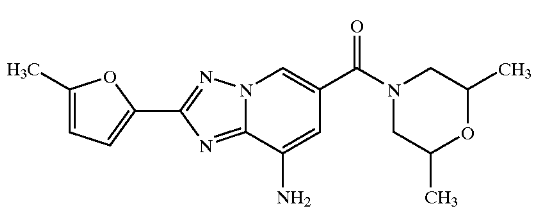 | [8-Amino-2-(5-methyl-furan-2-yl)-[1,2,4]triazolo[1,5-a]pyridin-6-yl]-(2,6-dimethyl-morpholin-4-yl)-methanone | 355.4 | MH$^+$ (100) |

-continued

| Ex. No. | hA2a K_i (nM) | hA1 K_i (nM) | Select. A1/A2a | Structure | Name | MW | MS m/e (%) |
|---|---|---|---|---|---|---|---|
| 93 | 321.6 | | | 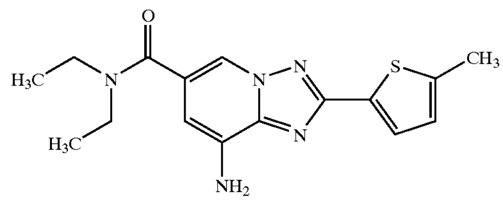 | 8-Amino-2-(5-methyl-thiophen-2-yl)-[1,2,4]triazolo[1,5-a]pyridine-6-carboxylic acid diethylamide | 329.4 | MH+ (100) |
| 94 | 212.8 | | | 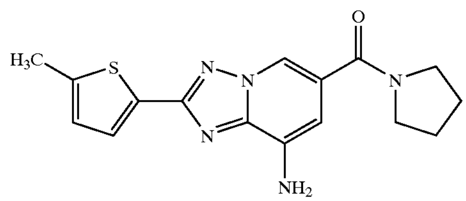 | [8-Amino-2-(5-methyl-thiophen-2-yl)-[1,2,4]triazolo[1,5-a]pyridin-6-yl]-pyrrolidin-1-yl-methanone | 327.4 | MH+ (100) |
| 95 | 225.4 | | | 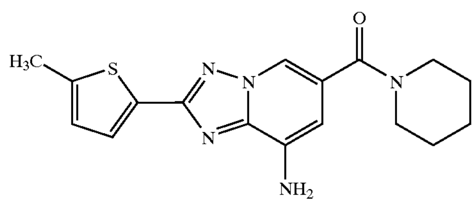 | [8-Amino-2-(5-methyl-thiophen-2-yl)-[1,2,4]triazolo[1,5-a]pyridin-6-yl]-piperidin-1-yl-methanone | 341.4 | MH+ (100) |
| 96 | 154.4 | | | 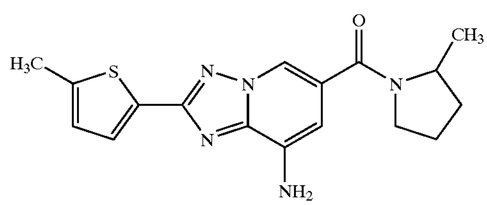 | [8-Amino-2-(5-methyl-thiophen-2-yl)-[1,2,4]triazolo[1,5-a]pyridin-6-yl]-(2-methyl-pyrrolidin-1-yl)-methanone | 341.4 | MH+ (100) |
| 97 | 427.6 | | | Chiral | [8-Amino-2-(5-methyl-thiophen-2-yl)-[1,2,4]triazolo[1,5-a]pyridin-6-yl]-((S)2-methoxymethyl-pyrrolidin-1-yl)-methanone | 371.5 | MH+ (100) |
| 98 | 219.6 | | | 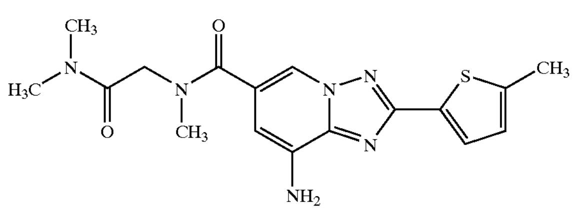 | 8-Amino-2-(5-methyl-thiophen-2-yl)-[1,2,4]triazolo[1,5-a]pyridine-6-carboxylic acid dimethylcarbamoyl-methyl-methyl-amide | 372.5 | MH+ (100) |
| 99 | 237.8 | | | 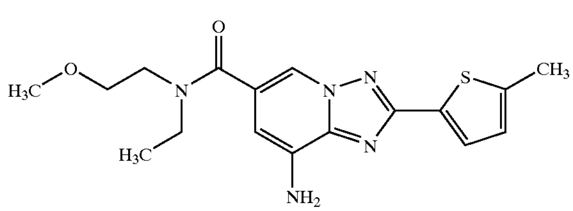 | 8-Amino-2-(5-methyl-thiophen-2-yl)-[1,2,4]triazolo[1,5-a]pyridine-6-carboxylic acid ethyl-(2-methoxy-ethyl)-amide | 359.5 | MH+ (100) |

-continued

| Ex. No. | hA2a K$_i$ (nM) | hA1 K$_i$ (nM) | Select. A1/A2a | Structure | Name | MW | MS m/e (%) |
|---|---|---|---|---|---|---|---|
| 100 | 178.2 | | | 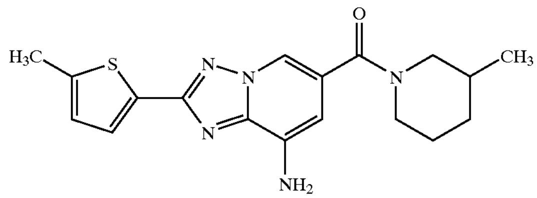 | [8-Amino-2-(5-methyl-thiophen-2-yl)-[1,2,4]triazolo[1,5-a]pyridin-6-yl]-(3-methyl-piperidin-1-yl)-methanone | 355.5 | MH$^+$ (100) |
| 101 | 228.2 | | | 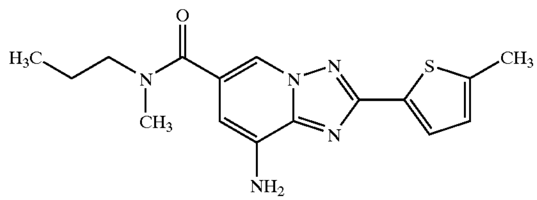 | 8-Amino-2-(5-methyl-thiophen-2-yl)-[1,2,4]triazolo[1,5-a]pyridine-6-carboxylic acid methyl-propyl-amide | 329.4 | MH$^+$ (100) |
| 102 | 478 | | | 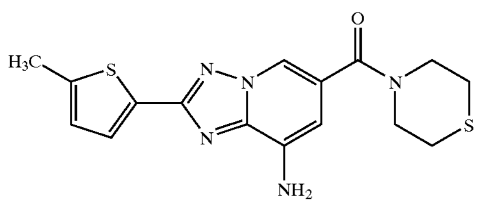 | [8-Amino-2-(5-methyl-thiophen-2-yl)-[1,2,4]triazolo[1,5-a]pyridin-6-yl]-thiomorpholin-4-yl-methanone | 359.5 | MH$^+$ (100) |
| 103 | 308.6 | | | 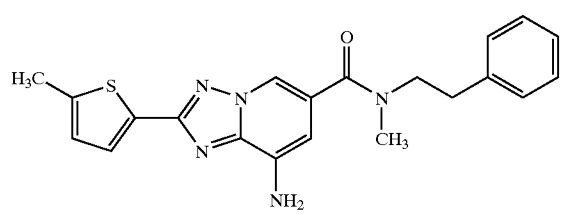 | 8-Amino-2-(5-methyl-thiophen-2-yl)-[1,2,4]triazolo[1,5-a]pyridine-6-carboxylic acid methyl-phenethyl-amide | 391.5 | MH$^+$ (100) |
| 104 | 564 | | | 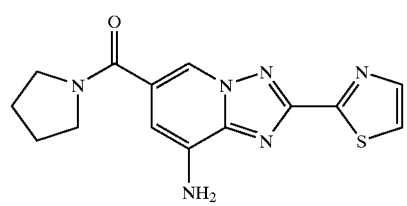 | (8-Amino-2-thiazol-2-yl-[1,2,4]triazolo[1,5-a]pyridin-6-yl)-pyrrolidin-1-yl-methanone | 314.4 | MH$^+$ (100) |
| 105 | 654 | | | 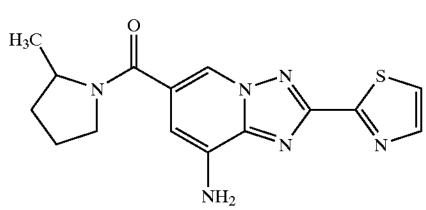 | (8-Amino-2-thiazol-2-yl-[1,2,4]triazolo[1,5-a]pyridin-6-yl)-(2-methyl-pyrrolidin-1-yl)-methanone | 328.4 | MH$^+$ (100) |
| 106 | 844 | | | 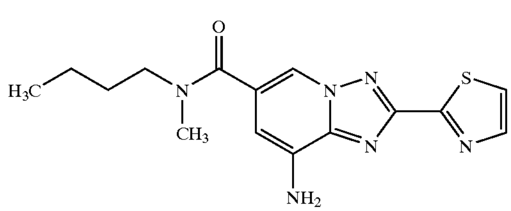 | 8-Amino-2-thiazol-2-yl-[1,2,4]triazolo[1,5-a]pyridine-6-carboxylic acid butyl-methyl-amide | 330.4 | MH$^+$ (100) |

| Ex. No. | hA2a $K_i$ (nM) | hA1 $K_i$ (nM) | Select. A1/A2a | Structure | Name | MW | MS m/e (%) |
|---|---|---|---|---|---|---|---|
| 107 | 632 | | | 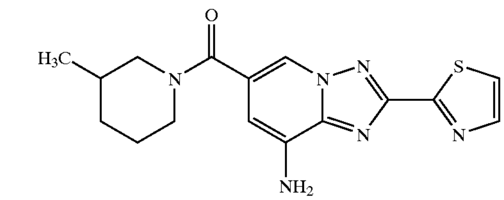 | (8-Amino-2-thiazol-2-yl-[1,2,4]triazolo[1,5-a]pyridin-6-yl)-(3-methyl-piperidin-1-yl)-methanone | 342.4 | MH+ (100) |
| 108 | 988 | | | 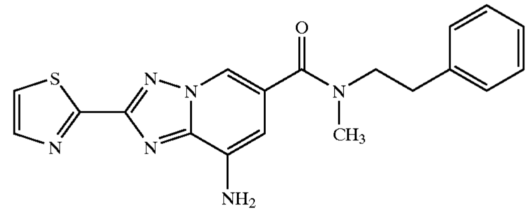 | 8-Amino-2-thiazol-2-yl-[1,2,4]triazolo[1,5-a]pyridine-6-carboxylic acid methyl-phenethyl-amide | 378.5 | MH+ (100) |

Tablet Formulation (Wet Granulation)

| | mg/tablet | | | |
|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure

1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | mg/capsule | | | |
|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2 and 3 in a suitable mixer for 30 minutes.
2. Add items 4 and 5 and mix for 3 minutes.
3. Fill into a suitable capsule.

What is claimed is:

1. A compound of the formula

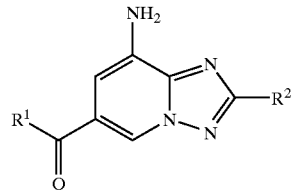

wherein

R$^1$ is —NR'R", wherein R' and R" are independently selected from the group consisting of lower alkyl, —(CH$_2$)$_n$—C(O)NR$^a$R$^b$, —(CH$_2$)$_n$-heteroaryl, —(CH$_2$)$_n$-aryl, —(CH$_2$)$_n$—CN, —(CH$_2$)$_n$—O-lower alkyl and —(CH$_2$)$_n$-cycloalkyl, or R' and R" form together with the N-atom a five or six-membered non-aromatic ring, containing no or one additional heteroatom selected from the group O and S, and said ring being unsubstituted or substituted by one or two substituents, selected from the group consisting of lower alkyl, —C(O)NR$^a$R$^b$ and —(CH$_2$)$_n$—O-lower alkyl and wherein R$^a$ and R$^b$ are independently selected from the group consisting of hydrogen and lower alkyl;

R$^2$ is selected from the group consisting of unsubstituted aryl, unsubstituted heteroaryl and aryl or heteroaryl substituted by lower alkyl or halogen; and n is 0, 1, 2 or 3;

or a pharmaceutically acceptable salt thereof.

2. The compound of claim 1, wherein R$^2$ is heteroaryl.

3. The compound of claim 2, wherein R$^2$ is furan-2-yl, substituted by bromo.

4. The compound of claim 3, wherein the compound is selected from the group consisting of

[8-amino-2-(5-bromo-furan-2-yl)-[1,2,4]triazolo[1,5-a]pyridin-6-yl]-piperidin-1-yl-methanone,

[8-amino-2-(5-bromo-furan-2-yl)-[1,2,4]triazolo[1,5-a]pyridin-6-yl]-pyrrolidin-1-yl-methanone,

[8-amino-2-(5-bromo-furan-2-yl)-[1,2,4]triazolo[1,5-a]pyridin-6-yl]-(2-methyl-pyrrolidin-1-yl)-methanone, 1-[8-amino-2-(5-bromo-furan-2-yl)-[1,2,4]triazolo[1,5-a]
  pyridine-6-carbonyl]-piperidine-3-carboxylic acid
  diethylamide,
[8-amino-2-(5-bromo-furan-2-yl)-[1,2,4]triazolo[1,5-a]
  pyridin-6-yl]-(3,5-dimethyl-piperidin-1-yl)-
  methanone,
[8-amino-2-(5-bromo-furan-2-yl)-[1,2,4]triazolo[1,5-a]
  pyridin-6-yl]-(2-methyl-piperidin-1-yl)-methanone,
[8-amino-2-(5-bromo-furan-2-yl)-[1,2,4]triazolo[1,5-a]
  pyridin-6-yl]-(2-methoxymethyl-pyrrolidin-1-yl)-
  methanone,
[8-amino-2-(5-bromo-furan-2-yl)-[1,2,4]triazolo[1,5-a]
  pyridin-6-yl]-((S)-2-methoxymethyl-pyrrolidin-1-yl)-
  methanone,
1-[8-amino-2-(5-bromo-furan-2-yl)-[1,2,4]triazolo[1,5-a]
  pyridine-6-carbonyl]-pyrrolidine-2-carboxylic acid
  (S)-dimethylamide,
8-amino-2-(5-bromo-furan-2-yl)-[1,2,4]triazolo[1,5-a]
  pyridine-6-carboxylic acid dimethylcarbamoylmethyl-
  methyl-amide,
[8-amino-2-(5-bromo-furan-2-yl)-[1,2,4]triazolo[1,5-a]
  pyridin-6-yl]-(3-methyl-piperidin-1-yl)-methanone,
8-amino-2-(5-bromo-furan-2-yl)-[1,2,4]triazolo[1,5-a]
  pyridine-6-carboxylic acid methyl-propyl-amide,
8-amino-2-(5-bromo-furan-2-yl)-[1,2,4]triazolo[1,5-a]
  pyridine-6-carboxylic acid ethyl-(2-pyridin-2-yl-
  ethyl)-amide,
[8-amino-2-(5-bromo-furan-2-yl)-[1,2,4]triazolo[1,5-a]
  pyridin-6-yl]-thiomorpholin-4-yl-methanone and
8-amino-2-(5-bromo-furan-2-yl)-[1,2,4]triazolo[1,5-a]
  pyridine-6-carboxylic acid methyl-phenethyl-amide.

5. The compound of claim 2, wherein $R^2$ is unsubstituted furan-2-yl.

6. The compound of claim 5, wherein the compound is selected from the group consisting of
  (8-amino-2-furan-2-yl-[1,2,4]triazolo[1,5-a]pyridin-6-yl)-pyrrolidin-1-yl-methanone,
  (8-amino-2-furan-2-yl-[1,2,4]triazolo[1,5-a]pyridin-6-yl)-(2-R-methoxymethyl-pyrrolidin-1-yl)-methanone,
  (8-amino-2-furan-2-yl-[1,2,4]triazolo[1,5-a]pyridin-6-yl)-(2-S-methoxymethyl-pyrrolidin-1-yl)-methanone and
  8-amino-2-furan-2-yl-[1,2,4]triazolo[1,5-a]pyridine-6-carboxylic acid dibenzylamide.

7. The compound of claim 2, wherein $R^2$ is thiophen-2-yl.

8. The compound of claim 7, wherein the compound is 8-amino-2-thiophen-2-yl-[1,2,4]triazolo[1,5-a]pyridine-6-carboxylic acid dibenzylamide.

9. The compound of claim 2, wherein $R^2$ is furan-2-yl, substituted by methyl.

10. The compound of claim 9, wherein the compound is selected from the group consisting of
  [8-amino-2-(5-methyl-furan-2-yl)-[1,2,4]triazolo[1,5-a]pyridin-6-yl]-pyrrolidin-1-yl-methanone,
  [8-amino-2-(5-methyl-furan-2-yl)-[1,2,4]triazolo[1,5-a]pyridin-6-yl]-piperidin-1-yl-methanone,
  [8-amino-2-(5-methyl-furan-2-yl)-[1,2,4]triazolo[1,5-a]pyridin-6-yl]-(2-methyl-pyrrolidin-1-yl)-methanone and
  8-amino-2-(5-methyl-furan-2-yl)-[1,2,4]triazolo[1,5-a]pyridine-6-carboxylic acid methyl-propyl-amide.

11. The compound of claim 1, wherein $R^2$ is aryl.

12. The compound of claim 11, wherein $R^2$ is phenyl.

13. A pharmaceutical composition comprising at least one compound of formula I of claim 1 and at least one pharmaceutically acceptable excipient.

14. A process for preparing a compound of formula I, comprising reacting a compound of formula

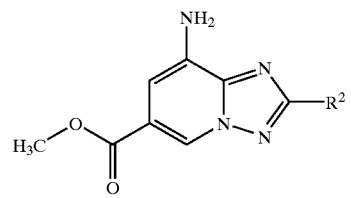

with an amine of formula

HNR'R"     III forming a compound of formula

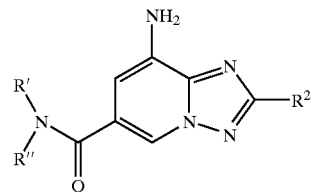

wherein $R^1$ is —NR'R", wherein R' and R" are independently selected from the group consisting of lower alkyl, —(CH$_2$)$_n$—C(O)NR$^a$R$^b$, —(CH$_2$)$_n$-heteroaryl, —(CH$_2$)$_n$-aryl, —(CH$_2$)$_n$—CN, —(CH$_2$)$_n$—O-lower alkyl and —(CH$_2$)$_n$-cycloalkyl, or R' and R" form together with the N-atom a five or six-membered non-aromatic ring, containing no or one additional O or S heteroatom, and said ring being unsubstituted or substituted by one or two substituents, selected from the group consisting of lower alkyl, —C(O)NR$^a$R$^b$ and —(CH$_2$)$_n$—O-lower alkyl and wherein R$^a$ and R$^b$ are independently selected from the group consisting of hydrogen and lower alkyl;

$R^2$ is selected from the group consisting of unsubstituted aryl, unsubstituted heteroaryl and aryl or heteroaryl substituted by lower alkyl or halogen; and n is 0, 1, 2 or 3.

15. A process of claim 14, further comprising adding a sufficient quantity of a pharmaceutically acceptable acid, thereby forming a pharmaceutically acceptable acid addition salt of the compound of formula I.

16. A method of treatment of depression or Parkinson's Disease comprising administering a therapeutically effective amount of a compound of formula I, or a pharmaceutically acceptable salt thereof, according to claim 1 to a person in need of such treatment.

* * * * *